US008624056B2

(12) United States Patent
Kelly et al.

(10) Patent No.: US 8,624,056 B2
(45) Date of Patent: Jan. 7, 2014

(54) HALOGENATED ANALOGUES OF ANTI-FIBROTIC AGENTS

(75) Inventors: Darren James Kelly, Wonga Park (AU); Spencer John Williams, Kensington (AU); Steven Zammit, Templestowe (AU)

(73) Assignee: Fibrotech Therapeutics Pty Ltd

( * ) Notice: Subject to any disclaimer, the term of this patent is extended or adjusted under 35 U.S.C. 154(b) by 602 days.

(21) Appl. No.: 12/809,751

(22) PCT Filed: Dec. 19, 2008

(86) PCT No.: PCT/AU2008/001868
§ 371 (c)(1),
(2), (4) Date: Oct. 5, 2010

(87) PCT Pub. No.: WO2009/079692
PCT Pub. Date: Jul. 2, 2009

(65) Prior Publication Data
US 2011/0021815 A1 Jan. 27, 2011
US 2012/0059188 A9 Mar. 8, 2012

Related U.S. Application Data

(60) Provisional application No. 61/016,134, filed on Dec. 21, 2007.

(51) Int. Cl.
*C07C 229/00* (2006.01)

(52) U.S. Cl.
USPC ......................................................... 562/450

(58) Field of Classification Search
None
See application file for complete search history.

(56) References Cited

U.S. PATENT DOCUMENTS

| | | | |
|---|---|---|---|
| 3,940,422 A | 2/1976 | Harita et al. | |
| 4,026,896 A | 5/1977 | Harita et al. | |
| 4,587,356 A | 5/1986 | Lizuka et al. | |
| 5,248,825 A | 9/1993 | Dinerstein et al. | |
| 5,356,620 A | 10/1994 | Yamamoto et al. | |
| 5,663,414 A | 9/1997 | Oinuma et al. | |
| 5,723,493 A | 3/1998 | Nagao et al. | |
| 6,127,392 A | 10/2000 | Lennox et al. | |
| 6,326,510 B1 | 12/2001 | Bernardon | |
| 6,646,009 B2 | 11/2003 | Reddy et al. | |
| 7,094,801 B2 | 8/2006 | Sikorski et al. | |
| 7,250,444 B2 | 7/2007 | Kennedy et al. | |
| 7,351,719 B2 | 4/2008 | Stenkamp et al. | |
| 7,592,373 B2 | 9/2009 | Lehmann-Lintz et al. | |
| 8,106,051 B2 | 1/2012 | Yamamori et al. | |
| 2002/0099089 A1 | 7/2002 | Hauel et al. | |
| 2005/0222423 A1 | 10/2005 | Saito et al. | |
| 2006/0014807 A1 | 1/2006 | Lin | |
| 2006/0089413 A1 | 4/2006 | Schmaus et al. | |
| 2007/0060646 A1 | 3/2007 | Gericke et al. | |
| 2007/0191378 A1 | 8/2007 | Campbell et al. | |
| 2007/0281969 A1 | 12/2007 | Colletti et al. | |
| 2007/0286892 A1 | 12/2007 | Herzberg et al. | |
| 2007/0299101 A1 | 12/2007 | Colletti et al. | |
| 2008/0008660 A1 | 1/2008 | Rabenhorst et al. | |
| 2008/0032983 A1 | 2/2008 | Gericke et al. | |
| 2009/0197957 A1 | 8/2009 | Selley et al. | |
| 2009/0226537 A1 | 9/2009 | Schmaus et al. | |
| 2010/0130497 A1* | 5/2010 | Williams et al. | 514/237.8 |
| 2011/0112187 A1 | 5/2011 | Schneider et al. | |
| 2011/0195977 A1 | 8/2011 | Fancelli et al. | |

FOREIGN PATENT DOCUMENTS

| | | |
|---|---|---|
| DE | 2402398 | 8/1974 |
| EP | 0816329 A1 | 1/1998 |
| EP | 0894496 A1 | 2/1999 |
| EP | 2185150 B1 | 3/2012 |
| JP | 50-135047 A | 10/1975 |
| JP | 50-140413 A | 11/1975 |
| JP | 51-001440 | 8/1976 |
| JP | 55-076852 A | 6/1980 |
| JP | 57-038759 A | 3/1982 |
| JP | 60-019754 A | 1/1985 |
| JP | 60-152454 A | 8/1985 |
| JP | 10259129 A | 9/1998 |
| JP | 10-306024 | 11/1998 |
| JP | 10-330254 | 12/1998 |
| JP | 2003-119132 A | 4/2003 |

(Continued)

OTHER PUBLICATIONS

First Office Action dated Jul. 6, 2012 in Japanese Application No. 2009-516828 and English-language translation.

(Continued)

*Primary Examiner* — Johann R Richter
*Assistant Examiner* — Jennifer C Sawyer
(74) *Attorney, Agent, or Firm* — Wolf, Greenfield & Sacks, P.C.

(57) ABSTRACT

The present invention relates to halogenated compounds of formula (I) with the substituents as described within the specification. The compounds may be useful as anti-fibrotic agents. The present invention also relates to methods for their preparation.

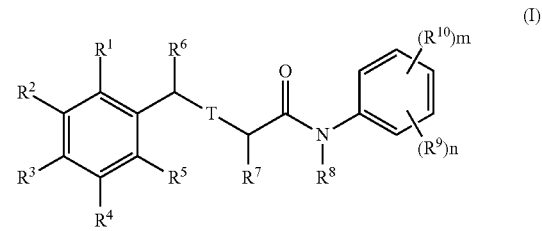

19 Claims, No Drawings

(56) References Cited

FOREIGN PATENT DOCUMENTS

| JP | 2007-509037 A | 4/2007 |
|---|---|---|
| JP | 2008-504241 A | 2/2008 |
| WO | WO 97/37650 A1 | 3/1997 |
| WO | WO 03/049702 A2 | 6/2003 |
| WO | WO 2004/047833 | 6/2004 |
| WO | WO 2006-053390 A1 | 5/2006 |
| WO | WO 2006/087393 A2 | 8/2006 |
| WO | WO 2006/102645 A1 | 9/2006 |
| WO | WO 2006/134120 A1 | 12/2006 |
| WO | WO 2007/015744 A1 | 2/2007 |
| WO | WO 2008/003141 A1 | 1/2008 |
| WO | WO 2008/051047 A1 | 5/2008 |
| WO | WO 2008/057862 A2 | 5/2008 |
| WO | WO 2009/068557 A1 | 6/2009 |
| WO | WO 2009/079692 A1 | 7/2009 |
| WO | WO 2009/082347 A1 | 7/2009 |

OTHER PUBLICATIONS

Supplementary Search Report from Singapore Patent Application 200900016-7, mailed Mar. 26, 2012.
[No Name Listed] "Expert Scientific Group on Phase One Clinical Trials Final Report", (Nov. 30, 2006), pp. C1, C35-C38.
Anari, M. R., et al., "Bridging cheminformatic metabolite predictions and tandem mass spectrometry", DDT (2005), vol. 10, pp. 711-717.
Bain, D. I., et al., "Synthesis of 2-Substituted -4H-3,1-benzoxazin-4-ones", J. Chem. Soc. (C), (1968), pp. 1593-1597.
Cancer Drug Design and Discovery Neidle, Stephen, ed. (Elsevier/Academic Press, 2008), p. 427.
Cheng, M. S. et al., "Synthesis of propenamides with anti-malarial activities and 3D-QSAR study", Acta Pharmaceutica Sinica, (2003), vol. 38, No. 7, pp. 505-510.
Collins, F. W., "Oat Phenolics: Avenanthramides, Novel Substituted N-Cinnamoylanthranilate Alkaloids from Oat Groats and Hulls", Agric. Food Chem., (1989), vol. 37, pp. 60-66.
Fura, A., "Role of pharmacologically active metabolites in drug discovery and development", DDT, (2006), vol. 11, pp. 133-142.
Gura, T., "Systems for Identifying New Drugs Are Often Faulty", Science, (Nov. 7, 1997) vol. 278, No. 5340, pp. 1041-1042.
Hajra, S., et al., "Lewis acid catalyzed intramolecular halo-arylation of tethered alkenes using N-halosuccinimide (NXS) as the halogen source; a general method for the synthesis of chromanones, chromans, quinolones, tetrahydroquinolines and tetralins", Tetrahedron Letters, (2005) vol. 46, No. 49, pp. 8599-8603.
International Preliminary Report on Patentability from corresponding International Application No. PCT/AU2008/001868, date of completion Mar. 25, 2010.
International Preliminary Report on Patentability from PCT/AU2007/000934, mailed Jan. 6, 2009.
International Search Report for International Application No. PCT/AU2008/001868, mailed Feb. 26, 2009.
International Search Report and Written Opinion from PCT/AU2007/000934, mailed Aug. 16, 2007.
Isaji, M., et al., "Selective Inhibition of Collagen Accumulation by N-(3,4- Dimethoxycinnamoyl)Anthranilic Acid (N-5') In Granulation Tissue," Biochemical Pharmacology, (1987), vol. 36, No. 4, pp. 469-474.
Ishihara, A., et al., "Induction of hydroxyanthranilate hydrocinnamoyl transferase activity by oligo-n-acethylchitooligosaccharides in oats", Phytochemistry, (1998), vol. 47, No. 6, pp. 969-674.
Kamb, A., "What's wrong with our cancer models?", Nature Reviews Drug Discovery, (Feb. 2005), vol. 4, pp. 161-165.
Leaf, C., "Why are we losing the war on cancer (and how to win it)", Health Administrator, (2005), vol. XVII, No. 1, pp. 172-183.
Luo, J., et al., "Principles of Cancer Therapy: Oncogene and Non-oncogene Addiction", Cell, (2009), vol. 136, pp. 823-837.
Merriam-Webster Online Dictionary entry for "analogue", (http://www.merriam-webster.com/dictionary/derivative), last accessed May 12, 2010.
Merriam-Webster Online Dictionary entry for "derivative", (http://www.merriam-webster.com/dictionary/derivative), last accessed Nov. 12, 2010.
Messiah, N. N., et al., "Synthesis of Some Benzoxazin-4-ones, Qinazolin-4-ones & Related Products", Indian Journal of Chemistry, (1975), vol. 13, pp. 326-328.
Nedderman, A. N. R., "Metabolites in Safety Testing: Metabolite Identification Strategies in Discovery and Development", Biopharm. Drug Dispos., (2009), vol. 30, pp. 152-162.
Ogita, H., et al., "Synthesis and structure-activity relationship of diarylamide derivatives as selective inhibitors of the proliferation of human coronary artery smooth muscle cells", Bioorg. Med. Chem. Lett., (2001), vol. 11, No. 4, pp. 549-551.
Okazaki, Y., et al., "Metabolism of avenanthramide phytoalexins in oats", the Plant Journal, (2004), vol. 39, pp. 560-657.
Patani et al., "Bioisosterism: a rational approach in drug design", Chem. Rev. vol. 96 (1996) pp. 3147-3176.
Rani, P., et al., "Isoxazolinyl derivatives of anthranilic acid as anti inflammatory agents", Indian Journal of Chemistry, Section B: Organic and Medicinal Chemistry, Council of Scientific and Industrial Research, IN, (2003), vol. 42, pp. 1729-1733.
STN File Registry, CAS Registry No. 475190-68-2, entered Dec. 5, 2002.
STN File Registry, CAS Registry No. 572907-40-5, entered Aug. 25, 2003.
STN File Registry, CAS Registry No. 850701-35-8, entered May 19, 2005.
STN File Registry, CAS Registry No. 875398-18-8, entered Feb. 27, 2006.
STN File Registry, CAS Registry No. 891611-78-2, entered Jul. 10, 2006.
STN File Registry, CAS Registry No. 900671-62-7, entered Aug. 11, 2006.
STN File Registry, CAS Registry No. 903317-85-1, entered Aug. 22, 2006.
STN File Registry, CAS Registry No. 926525-60-2, entered Mar. 15, 2007.
STN File Registry, CAS Registry No. 926872-74-4, entered Mar. 18, 2007.
STN File Registry, CAS Registry No. 930720-96-0, entered Apr. 18, 2007.
STN File Registry, CAS Registry No. 931079-11-7, entered Apr. 20, 2007.
STN File Registry, CAS Registry No. 938782-52-6, entered Jun. 25, 2007.
Search Report and Written Opinion from Singapore Application No. 200900016-7, mailed Oct. 14, 2010.
Supplementary European Search Report for European Application No. 07 76 3756 dated Jan. 13, 2011.
Supplementary Search Report from corresponding European Application No. 08865709.3, mailed Jan. 19, 2011.
Written Opinion of the International Searching Authority for International Application No. PCT/AU2008/001868, mailed Feb. 26, 2009.
First Office Action dated Oct. 1, 2013 in Japanese Application No. 2010-538278.

* cited by examiner

HALOGENATED ANALOGUES OF ANTI-FIBROTIC AGENTS

RELATED APPLICATIONS

The present application is a national stage filing under 35 U.S.C. §371 of International Application No. PCT/AU2008/001868, filed on 19 Dec. 2008, which claims priority from U.S. provisional patent application No. 61/016,134 filed on 21 Dec. 2007, the contents of each of which are herein incorporated by reference.

FIELD

The present invention relates to derivatives of the anti-fibrotic drug, tranilast. More particularly, the present invention relates to halogenated cinnamoylbenzamide derivatives.

BACKGROUND

Anti-inflammatory agents have been used to treat fibrosis with the aim of suppressing chronic inflammation, but such treatments can be unsatisfactory in terms of efficacy and side effects. Numerous studies have been performed to obtain substances that inhibit the production or the activity of the cytokines thought to be involved in fibrosis. Tranilast (n-[3,4-dimethoxycinnamoyl] anthranilic acid; product name Rizaben™) is an anti-fibrotic agent used in Japan for the treatment of fibrotic skin disorders such as keloids and scleroderma. Although the precise mechanisms and mode of action of tranilast are incompletely understood, its ability to inhibit ERK phosphorylation, a major intermediate in the TGF-β signalling pathway, may underlie its antifibrotic effects, with known actions of tranilast including the inhibition of TGF-β-induced extracellular matrix production in a range of cell types. Tranilast has also been shown to attenuate TGF-β-induced collagen synthesis in cardiac fibroblasts using an experimental model of diabetic cardiac disease, and to reduce inflammation in allergic diseases, such as allergic rhinitis and bronchial asthma, etc. In addition, tranilast has been shown to have anti-proliferative activity.

However, it has recently been shown that genetic factors in certain patients may confer susceptibility to tranilast-induced hyperbilirubinemia. One possibility for how this may arise is the presence of Gilbert's syndrome polymorphisms of the glucuronosyltransferase UGT1A1, which leads to increased susceptibility to tranilast-induced hyperbilirubinemia. Such hyperbilirubinemia may result from the low level of UGT1A1 glucuronosyltransferase present in individuals with this syndrome. Tranilast itself, and its major metabolite N3 (4-desmethyl-tranilast), have been shown to be inhibitors of UGT1A1, potentially leading to aberrant metabolism of bilirubin and its accumulation.

Accordingly, compounds that are based on tranilast have the potential to provide compounds that may have pharmaceutical properties with potential anti-fibrotic, anti-inflammatory, and anti-proliferative or anti-neoplastic activity, and as alternatives/adjuncts to tranilast. These compounds may also have altered and/or improved metabolism relative to tranilast.

SUMMARY

The present invention provides a compound of Formula (I)

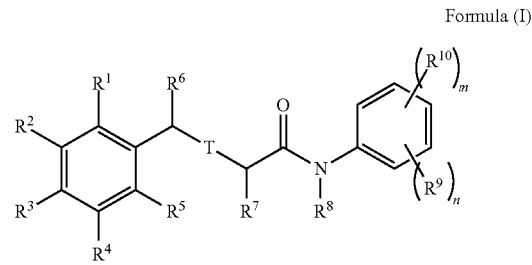

Formula (I)

or a pharmaceutically acceptable salt or prodrug thereof, wherein:

T is a single bond, a double bond or a triple bond;

$R^1$, $R^2$, $R^3$, $R^4$, and $R^5$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl; provided that at least one of $R^1$, $R^2$, $R^3$, $R^4$, and $R^5$ contains a halogen;

$R^6$ and $R^7$ are present when T is a single bond or a double bond but not when T is a triple bond, each $R^6$ and $R^7$ being independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, COOH, COOR¹¹, CONR¹¹R¹², NR¹¹COR¹², NR¹¹COOR¹², NR¹¹SO₂R¹², NR¹¹CONR¹²R¹³, NR¹¹R¹², and acyl;

R⁸ is selected from the group consisting of: H, a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

R⁹ is selected from the group consisting of: H, COOR¹¹, CONR¹¹R¹², COSR¹¹, OR¹¹, NR¹¹R¹², and SR¹¹;

R¹⁰ is selected from the group consisting of: H, halogen, OH, NO₂, CN, NH₂, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, SR¹¹, SO₃H, SO₂NR¹¹R¹², SO₂R¹¹, SONR¹¹R¹², SOR¹¹, COR¹¹, COOH, COOR¹¹, CONR¹¹R¹², NR¹¹COR¹², NR¹¹COOR¹², NR¹¹SO₂R¹², NR¹¹CONR¹²R¹³, NR¹¹R¹², and acyl;

each R¹¹, R¹² and R¹³ is independently selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

m is an integer selected from the group consisting of 0, 1, 2, 3, and 4;

n is an integer selected from the group consisting of 1, 2, 3, and 4, and 5; and m+n is an integer selected from the group consisting of 1, 2, 3, 4, and 5.

As with any group of structurally related compounds which possess a particular utility, certain embodiments of variables of the compounds of the Formula (I), may be particularly useful in their end use application.

In some embodiments at least one of R¹, R², R³, R⁴, and R⁵ is selected from the group consisting of $C_1$-$C_{12}$ alkyloxy containing at least one halogen atom, $C_1$-$C_{12}$ alkenyloxy containing at least one halogen atom, and $C_1$-$C_{12}$ alkynyloxy containing at least one halogen atom. In some embodiments, the $C_1$-$C_{12}$ alkyloxy group is of Formula (II):

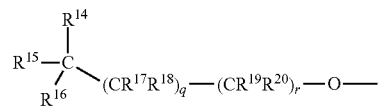

Formula (II)

wherein:
R¹⁴, R¹⁵, and R¹⁶ are each independently selected from the group consisting of: H, halogen, OH, NO₂, CN, NH₂, optionally substituted $C_1$-$C_{12}$ alkyl, and optionally substituted $C_2$-$C_{12}$ alkenyl;

R¹⁷, R¹⁸, R¹⁹, and R²⁰ are each independently selected from the group consisting of: H, halogen, OH, NO₂, CN, and NH₂;

at least one of R¹⁴, R¹⁵, R¹⁶, R¹⁷, R¹⁸, R¹⁹, and R²⁰ is or contains a halogen atom;

q is an integer selected from the group consisting of: 0, 1, 2, 3, 4, 5, 6, 7, 8, 9, and 10; and r is an integer selected from the group consisting of: 0, 1, 2, 3, 4, 5, 6, 7, 8, 9, and 10.

In some embodiments q and r are 0, and at least two of R¹⁴, R¹⁵, and R¹⁶ are a halogen.

The halogen may be selected from the group consisting of: fluorine, chlorine, bromine, and iodine. In some embodiments the halogen is fluorine.

In some embodiments at least one of R¹, R², R³, R⁴, and R⁵ is the group —O—CHF₂. In some embodiments R³ is the group —O—CHF₂. In some embodiments R² and R³ are the group —O—CHF₂.

In some embodiments T is a double bond or a triple bond.

In some embodiments R⁹ is selected from the group consisting of: COOR¹¹ and CONR¹¹R¹². In some embodiments R⁹ is selected from the group consisting of: COOH, CONH₂, and CONHCH₃.

In some embodiments R⁹ is NR¹¹R¹². In some embodiments R⁹ is NH₂.

In some embodiments n is 1.

In some embodiments R¹⁰ is halogen.

In another aspect the present invention provides a compound of Formula (III)

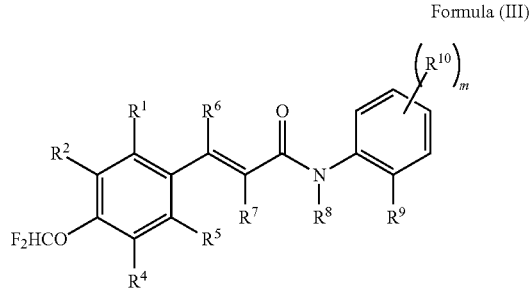

Formula (III)

or a pharmaceutically acceptable salt or prodrug thereof, wherein:

R¹, R², R⁴, and R⁵ are each independently selected from the group consisting of: H, halogen, OH, NO₂, CN, NH₂, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted C₁-C₁₈ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl; provided that at least one of $R^1$, $R^2$, $R^3$, $R^4$, and $R^5$ contains a halogen atom;

$R^6$ and $R^7$ are each independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl $R^8$ is selected from the group consisting of: H, a N-protecting group, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{10}$heteroalkyl, optionally substituted $C_3$-$C_{12}$cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$aryl, and optionally substituted $C_1$-$C_{18}$heteroaryl;

$R^9$ is selected from the group consisting of: $COOR^{11}$, $CONR^{11}R^{12}$, and $NR^{11}R^{12}$;

$R^{10}$ is selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl;

each $R^{11}$, $R^{12}$ and $R^{13}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{10}$heteroalkyl, optionally substituted $C_3$-$C_{12}$cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$aryl, and optionally substituted $C_1$-$C_{18}$heteroaryl; and m is an integer selected from the group consisting of 0, 1, 2, 3, and 4.

In some embodiments $R^2$ is the group —O—$CHF_2$.

In some embodiments $R^2$ is selected from the group consisting of: optionally substituted $C_1$-$C_{12}$ alkyloxy and optionally substituted $C_2$-$C_{12}$ alkynyloxy.

In some embodiments $R^1$ is the group —O—$CHF_2$.
In some embodiments $R^4$ is the group —O—$CHF_2$.
In some embodiments $R^5$ is the group —O—$CHF_2$.

In some embodiments $R^1$ is selected from the group consisting of: optionally substituted $C_1$-$C_{12}$ alkyloxy and optionally substituted $C_2$-$C_{12}$ alkynyloxy.

In some embodiments $R^4$ is selected from the group consisting of: optionally substituted $C_1$-$C_{12}$ alkyloxy and optionally substituted $C_2$-$C_{12}$ alkynyloxy.

In some embodiments $R^5$ is selected from the group consisting of: optionally substituted $C_1$-$C_{12}$ alkyloxy and optionally substituted $C_2$-$C_{12}$ alkynyloxy.

In some embodiments $R^6$ and $R^7$ are each independently selected from the group consisting of: H, and optionally substituted $C_1$-$C_{12}$ alkyl.

In some embodiments $R^6$ is $CH_3$.
In some embodiments $R^7$ is $CH_3$.
In some embodiments $R^8$ is H.

In some embodiments $R^9$ is selected from the group consisting of: $COOR^{11}$ and $CONR^{11}R^{12}$. In some embodiments $R^9$ is selected from the group consisting of: COOH, $CONH_2$, and $CONHCH_3$.

In some embodiments $R^9$ is $NR^{11}R^{12}$. In some embodiments $R^9$ is $NH_2$.

In some embodiments $R^{10}$ is a halogen.

In some embodiments m is 1.

In another aspect the present invention provides a compound of Formula (IV)

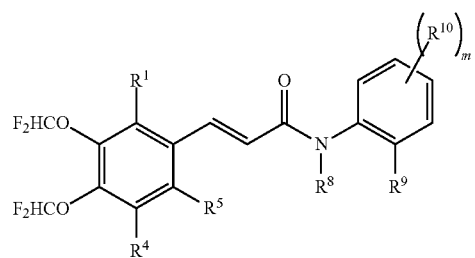

Formula (IV)

or a pharmaceutically acceptable salt or prodrug thereof, wherein:
R$^1$, R$^4$, and R$^5$ are each independently selected from the group consisting of: H, halogen, OH, NO$_2$, CN, NH$_2$, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_2$-C$_{12}$ heterocycloalkyl, optionally substituted C$_2$-C$_{12}$ heterocycloalkenyl, optionally substituted C$_6$-C$_{18}$ aryl, optionally substituted C$_1$-C$_{18}$ heteroaryl, optionally substituted C$_1$-C$_{12}$ alkyloxy, optionally substituted C$_2$-C$_{12}$ alkenyloxy, optionally substituted C$_2$-C$_{12}$ alkynyloxy, optionally substituted C$_1$-C$_{10}$ heteroalkyloxy, optionally substituted C$_3$-C$_{12}$ cycloalkyloxy, optionally substituted C$_3$-C$_{12}$ cycloalkenyloxy, optionally substituted C$_1$-C$_{12}$ heterocycloalkyloxy, optionally substituted C$_1$-C$_{12}$ heterocycloalkenyloxy, optionally substituted C$_6$-C$_{18}$ aryloxy, optionally substituted C$_1$-C$_{18}$ heteroaryloxy, optionally substituted C$_1$-C$_{12}$ alkylamino, SR$^{11}$, SO$_3$H, SO$_2$NR$^{11}$R$^{12}$, SO$_2$R$^{11}$, SONR$^{11}$R$^{12}$, SOR$^{11}$, COR$^{11}$, COOH, COOR$^{11}$, CONR$^{11}$R$^{12}$, NR$^{11}$COR$^{12}$, NR$^{11}$COOR$^{12}$, NR$^{11}$SO$_2$R$^{12}$, NR$^{11}$CONR$^{12}$R$^{13}$, NR$^{11}$R$^{12}$, and acyl; provided that at least one of R$^1$, R$^2$, R$^3$, R$^4$, and R$^5$ contains a halogen atom;

R$^8$ is selected from the group consisting of: H, a N-protecting group, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_1$-C$_{12}$ heterocycloalkyl, optionally substituted C$_1$-C$_{12}$ heterocycloalkenyl, optionally substituted C$_6$-C$_{18}$ aryl, and optionally substituted C$_1$-C$_{18}$ heteroaryl;

R$^9$ is selected from the group consisting of: COOR$^{11}$, CONR$^{11}$R$^{12}$, and NR$^{11}$R$^{12}$;

R$^{10}$ is selected from the group consisting of: H, halogen, OH, NO$_2$, CN, NH$_2$, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_2$-C$_{12}$ heterocycloalkyl, optionally substituted C$_2$-C$_{12}$ heterocycloalkenyl, optionally substituted C$_6$-C$_{18}$ aryl, optionally substituted C$_1$-C$_{18}$ heteroaryl, optionally substituted C$_1$-C$_{12}$ alkyloxy, optionally substituted C$_2$-C$_{12}$ alkenyloxy, optionally substituted C$_2$-C$_{12}$ alkynyloxy, optionally substituted C$_1$-C$_{10}$ heteroalkyloxy, optionally substituted C$_3$-C$_{12}$ cycloalkyloxy, optionally substituted C$_3$-C$_{12}$ cycloalkenyloxy, optionally substituted C$_1$-C$_{12}$ heterocycloalkyloxy, optionally substituted C$_1$-C$_{12}$ heterocycloalkenyloxy, optionally substituted C$_6$-C$_{18}$ aryloxy, optionally substituted C$_1$-C$_{18}$ heteroaryloxy, optionally substituted C$_1$-C$_{12}$ alkylamino, SR$^{11}$, SO$_3$H, SO$_2$NR$^{11}$R$^{12}$, SO$_2$R$^{11}$, SONR$^{11}$R$^{12}$, SOR$^{11}$, COR$^{11}$, COOH, COOR$^{11}$, CONR$^{11}$R$^{12}$, NR$^{11}$COR$^{12}$, NR$^{11}$COOR$^{12}$, NR$^{11}$SO$_2$R$^{12}$, NR$^{11}$CONR$^{12}$R$^{13}$, NR$^{11}$R$^{12}$, and acyl;

each R$^{11}$, R$^{12}$ and R$^{13}$ is independently selected from the group consisting of H, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_1$-C$_{12}$ heterocycloalkyl, optionally substituted C$_1$-C$_{12}$ heterocycloalkenyl, optionally substituted C$_6$-C$_{18}$ aryl, and optionally substituted C$_1$-C$_{18}$ heteroaryl; and m is an integer selected from the group consisting of: 0, 1, 2, 3, and 4.

In some embodiments R$^1$ is the group —O—CHF$_2$.
In some embodiments R$^4$ is the group —O—CHF$_2$.
In some embodiments R$^5$ is the group —O—CHF$_2$.
In some embodiments R$^1$ is selected from the group consisting of: optionally substituted C$_1$-C$_{12}$ alkyloxy and optionally substituted C$_2$-C$_{12}$ alkynyloxy.
In some embodiments R$^4$ is selected from the group consisting of: optionally substituted C$_1$-C$_{12}$ alkyloxy and optionally substituted C$_2$-C$_{12}$ alkynyloxy.
In some embodiments R$^5$ is selected from the group consisting of: optionally substituted C$_1$-C$_{12}$ alkyloxy and optionally substituted C$_2$-C$_{12}$ alkynyloxy.
In some embodiments R$^6$ and R$^7$ are each independently selected from the group consisting of: H, and optionally substituted C$_1$-C$_{12}$ alkyl.
In some embodiments R$^6$ is CH$_3$.
In some embodiments R$^7$ is CH$_3$.
In some embodiments R$^8$ is H.
In some embodiments R$^9$ is selected from the group consisting of: COOR$^{11}$ and CONR$^{11}$R$^{12}$. In some embodiments R$^9$ is selected from the group consisting of: COOH, CONH$_2$, and CONHCH$_3$.
In some embodiments R$^9$ is NR$^{11}$R$^{12}$. In some embodiments R$^9$ is NH$_2$.
In some embodiments R$^{10}$ is a halogen.
In some embodiments m is 1.
In another aspect the present invention provides a compound of Formula (V)

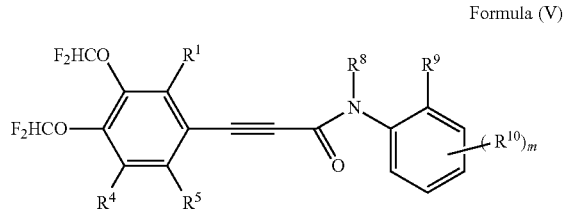

Formula (V)

or a pharmaceutically acceptable salt or prodrug thereof, wherein:
R$^1$, R$^4$, and R$^5$ are each independently selected from the group consisting of: H, halogen, OH, NO$_2$, CN, NH$_2$, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_2$-C$_{12}$ heterocycloalkyl, optionally substituted C$_2$-C$_{12}$ heterocycloalkenyl, optionally substituted C$_6$-C$_{18}$ aryl, optionally substituted C$_1$-C$_{18}$ heteroaryl, optionally substituted C$_1$-C$_{12}$ alkyloxy, optionally substituted C$_2$-C$_{12}$ alkenyloxy, optionally substituted C$_2$-C$_{12}$ alkynyloxy, optionally substituted C$_1$-C$_{10}$ heteroalkyloxy, optionally substituted C$_3$-C$_{12}$ cycloalkyloxy, optionally substituted C$_3$-C$_{12}$ cycloalkenyloxy, optionally substituted C$_1$-C$_{12}$ heterocycloalkyloxy, optionally substituted C$_1$-C$_{12}$ heterocycloalkenyloxy, optionally substituted C$_6$-C$_{18}$ aryloxy, optionally substituted C$_1$-C$_{18}$ heteroaryloxy, optionally substituted C$_1$-C$_{12}$ alkylamino, SR$^{11}$, SO$_3$H, SO$_2$NR$^{11}$R$^{12}$, SO$_2$R$^{11}$, SONR$^{11}$R$^{12}$, SOR$^{11}$, COR$^{11}$, COOH, COOR$^{11}$, CONR$^{11}$R$^{12}$, NR$^{11}$COR$^{12}$, NR$^{11}$COOR$^{12}$, NR$^{11}$SO$_2$R$^{12}$, NR$^{11}$CONR$^{12}$R$^{13}$, NR$^{11}$R$^{12}$, and acyl; provided that at least one of R$^1$, R$^2$, R$^3$, R$^4$, and R$^5$ contains a halogen atom;

R$^8$ is selected from the group consisting of: H, a N-protecting group, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_1$-C$_{12}$ heterocycloalkyl, optionally substituted C$_1$-C$_{12}$ heterocycloalkenyl, optionally substituted C$_6$-C$_{18}$ aryl, and optionally substituted C$_1$-C$_{18}$ heteroaryl;

R$^9$ is selected from the group consisting of: COOR$^{11}$, CONR$^{11}$R$^{12}$, and NR$^{11}$R$^{12}$;

R$^{10}$ is selected from the group consisting of: H, halogen, OH, NO$_2$, CN, NH$_2$, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_2$-C$_{12}$ heterocycloalkyl, optionally substituted C$_2$-C$_{12}$ heterocycloalkenyl, optionally substituted C$_6$-C$_{18}$ aryl, optionally substituted C$_1$-C$_{18}$ heteroaryl, optionally substituted C$_1$-C$_{12}$ alkyloxy, optionally substituted C$_2$-C$_{12}$ alkenyloxy, optionally substituted C$_2$-C$_{12}$ alkynyloxy, optionally substituted C$_1$-C$_{10}$ heteroalkyloxy, optionally substituted C$_3$-C$_{12}$ cycloalkyloxy, optionally substituted C$_3$-C$_{12}$ cycloalkenyloxy, optionally substituted C$_1$-C$_{12}$ heterocycloalkyloxy, optionally substituted C$_1$-C$_{12}$ heterocycloalkenyloxy, optionally substituted C$_6$-C$_{18}$ aryloxy, optionally substituted C$_1$-C$_{18}$ heteroaryloxy, optionally substituted C$_1$-C$_{12}$ alkylamino, SR$^{11}$, SO$_3$H, SO$_2$NR$^{11}$R$^{12}$, SO$_2$R$^{11}$, SONR$^{11}$R$^{12}$, SOR$^{11}$, COR$^{11}$, COOH, COOR$^{11}$, CONR$^{11}$R$^{12}$, NR$^{11}$COR$^{12}$, NR$^{11}$COOR$^{12}$, NR$^{11}$SO$_2$R$^{12}$, NR$^{11}$CONR$^{12}$R$^{13}$, NR$^{11}$R$^{12}$, and acyl;

each R$^{11}$, R$^{12}$ and R$^{13}$ is independently selected from the group consisting of H, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_1$-C$_{12}$ heterocycloalkyl, optionally substituted C$_1$-C$_{12}$ heterocycloalkenyl, optionally substituted C$_6$-C$_{18}$aryl, and optionally substituted C$_1$-C$_{18}$ heteroaryl; and m is an integer selected from the group consisting of 0, 1, 2, 3, and 4.

In some embodiments R$^1$ is the group —O—CHF$_2$, R$^4$ and R$^5$ are H, whilst in other embodiments R$^4$ is the group —O—CHF$_2$, R$^1$ and R$^5$ are H. In still other embodiments R$^5$ is the group —O—CHF$_2$, R$^1$ and R$^4$ are H.

In some embodiments R$^8$ is H.

In some embodiments R$^9$ is selected from the group consisting of: COOR$^{11}$ and CONR$^{11}$R$^{12}$. In some embodiments R$^9$ is selected from the group consisting of: COOH, CONH$_2$, and CONHCH$_3$.

In some embodiments R$^9$ is NR$^{11}$R$^{12}$. In some embodiments R$^9$ is NH$_2$.

In some embodiments R$^{10}$ is a halogen.

In some embodiments m is 1.

Specific embodiments of the invention provide compounds selected from the group consisting of:

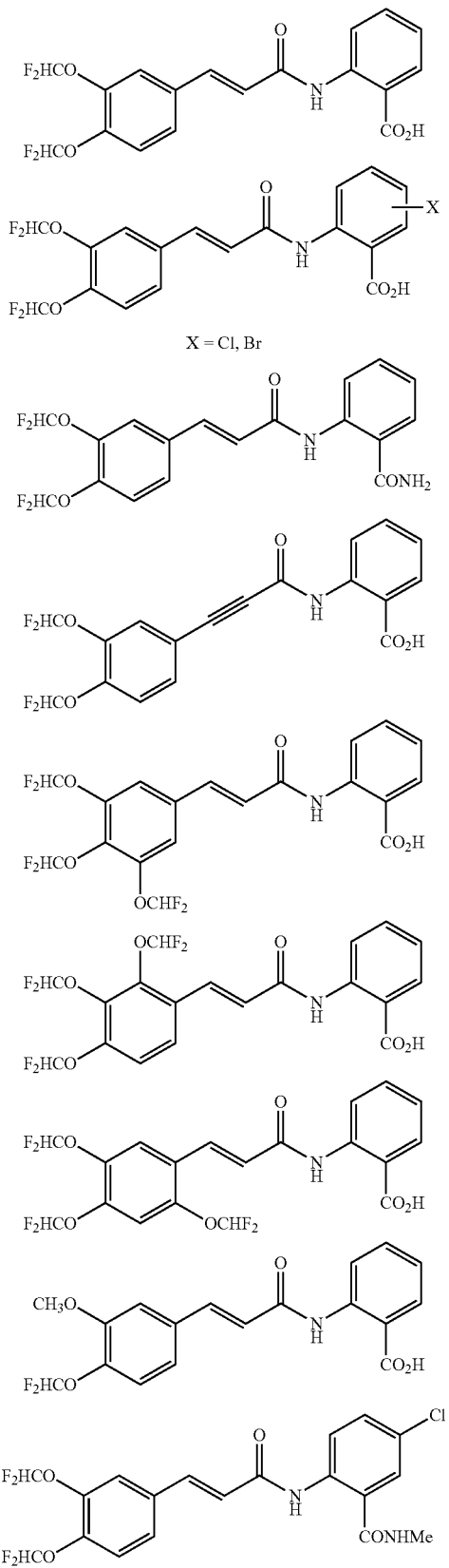

-continued

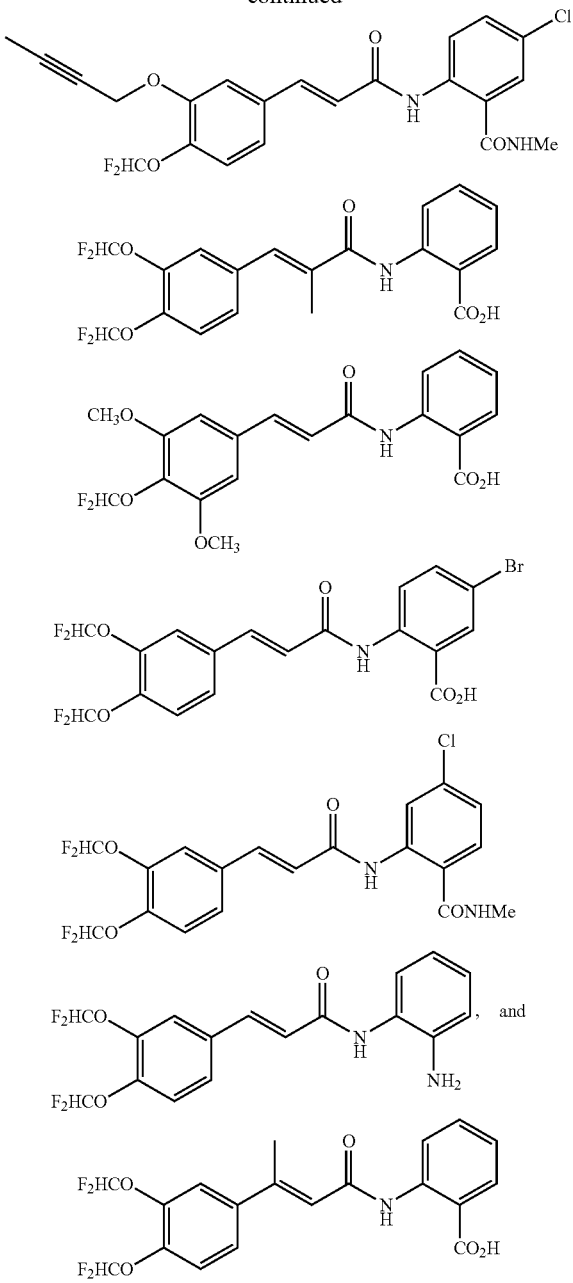

or a pharmaceutically acceptable salt or prodrug thereof.

In addition to compounds of Formulae I, III, and IV, the embodiments disclosed are also directed to pharmaceutically acceptable salts, pharmaceutically acceptable N-oxides, pharmaceutically acceptable prodrugs, and pharmaceutically active metabolites of such compounds, and pharmaceutically acceptable salts of such metabolites.

The compounds of the present invention may have anti-fibrotic, anti-inflammatory, anti-proliferative or anti-neoplastic activity and may, therefore, find use as an alternative and/or adjunct to tranilast.

DETAILED DESCRIPTION

In this specification a number of terms are used which are well known to a skilled addressee. Nevertheless for the purposes of clarity a number of terms will be defined.

As used herein, the term unsubstituted means that there is no substituent or that the only substituents are hydrogen.

The term "optionally substituted" as used throughout the specification denotes that the group may or may not be further substituted or fused (so as to form a polycyclic system), with one or more non-hydrogen substituent groups. In certain embodiments the substituent groups are one or more groups independently selected from the group consisting of halogen, =O, =S, —CN, —NO$_2$, —CF$_3$, —OCF$_3$, —OCHF$_2$, alkyl, alkenyl, alkynyl, haloalkyl, haloalkenyl, haloalkynyl, heteroalkyl, cycloalkyl, cycloalkenyl, heterocycloalkyl, heterocycloalkenyl, aryl, heteroaryl, cycloalkylalkyl, heterocycloalkylalkyl, heteroarylalkyl, arylalkyl, cycloalkylalkenyl, heterocycloalkylalkenyl, arylalkenyl, heteroarylalkenyl, cycloalkylheteroalkyl, heterocycloalkylheteroalkyl, arylheteroalkyl, heteroarylheteroalkyl, hydroxy, hydroxyalkyl, alkoxy, alkoxyalkyl, alkoxycycloalkyl, alkoxyheterocycloalkyl, alkoxyaryl, alkoxyheteroaryl, alkoxycarbonyl, alkylaminocarbonyl, alkenyloxy, alkynyloxy, cycloalkyloxy, cycloalkenyloxy, heterocycloalkyloxy, heterocycloalkenyloxy, aryloxy, phenoxy, benzyloxy, heteroaryloxy, arylalkyloxy, arylalkyl, heteroarylalkyl, cycloalkylalkyl, heterocycloalkylalkyl, arylalkyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, alkylsulfinyl, arylsulfinyl, aminosulfinylaminoalkyl, —COOH, —COR$^{11}$, —C(O)OR$^{11}$, CONHR$^{11}$, NHCOR$^{11}$, NHCOOR$^{11}$, NHCONHR$^{11}$, C(=NOH)R$^{11}$, —SH, —SR$^{11}$, —OR$^{11}$, and acyl, wherein R$^{11}$ is H, optionally substituted C$_1$-C$_{12}$alkyl, optionally substituted C$_2$-C$_{12}$alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_1$-C$_{12}$ heterocycloalkyl, optionally substituted C$_1$-C$_{12}$ heterocycloalkenyl, optionally substituted C$_6$-C$_{18}$ aryl, optionally substituted C$_1$-C$_{18}$ heteroaryl, and acyl.

"Alkyl" as a group or part of a group refers to a straight or branched aliphatic hydrocarbon group, such as a C$_1$-C$_{14}$ alkyl, a C$_1$-C$_{10}$ alkyl or a C$_1$-C$_6$ unless otherwise noted. Examples of suitable straight and branched C$_1$-C$_6$ alkyl substituents include methyl, ethyl, n-propyl, 2-propyl, n-butyl, sec-butyl, t-butyl, hexyl, and the like. The group may be a terminal group or a bridging group.

"Alkylamino" includes both mono-alkylamino and dialkylamino, unless specified. "Mono-alkylamino" means a —NH-Alkyl group, in which alkyl is as defined above. "Dialkylamino" means a —N(alkyl)$_2$ group, in which each alkyl may be the same or different and are each as defined herein for alkyl. The alkyl group may be a C$_1$-C$_6$ alkyl group. The group may be a terminal group or a bridging group.

"Arylamino" includes both mono-arylamino and di-arylamino unless specified. Mono-arylamino means a group of formula arylNH—, in which aryl is as defined herein. Di-arylamino means a group of formula (aryl)$_2$N— where each aryl may be the same or different and are each as defined herein for aryl. The group may be a terminal group or a bridging group.

"Acyl" means an alkyl-CO— group in which the alkyl group is as described herein. Examples of acyl include acetyl and benzoyl. The alkyl group may be a C$_1$-C$_6$ alkyl group. The group may be a terminal group or a bridging group.

"Alkenyl" as a group or part of a group denotes an aliphatic hydrocarbon group containing at least one carbon-carbon double bond and which may be straight or branched such as a group having 2-14 carbon atoms, 2-12 carbon atoms, or 2-6 carbon atoms, in the normal chain. The group may contain a plurality of double bonds in the normal chain and the orientation about each is independently E or Z. Exemplary alkenyl groups include, but are not limited to, ethenyl, propenyl, butenyl, pentenyl, hexenyl, heptenyl, octenyl and nonenyl. The group may be a terminal group or a bridging group.

"Alkoxy" refers to an —O-alkyl group in which alkyl is defined herein. The alkoxy may be a $C_1$-$C_6$ alkoxy. Examples include, but are not limited to, methoxy and ethoxy. The group may be a terminal group or a bridging group.

"Alkenyloxy" refers to an —O— alkenyl group in which alkenyl is as defined herein. Preferred alkenyloxy groups are $C_2$-$C_6$ alkenyloxy groups. The group may be a terminal group or a bridging group.

"Alkynyloxy" refers to an —O-alkynyl group in which alkynyl is as defined herein. Preferred alkynyloxy groups are $C_2$-$C_6$ alkynyloxy groups. The group may be a terminal group or a bridging group.

"Alkoxycarbonyl" refers to an —C(O)—O-alkyl group in which alkyl is as defined herein. The alkyl group may be a $C_1$-$C_6$ alkyl group. Examples include, but not limited to, methoxycarbonyl and ethoxycarbonyl. The group may be a terminal group or a bridging group.

"Alkylsulfinyl" means a —S(O)-alkyl group in which alkyl is as defined above. The alkyl group is preferably a $C_1$-$C_6$ alkyl group. Exemplary alkylsulfinyl groups include, but not limited to, methylsulfinyl and ethylsulfinyl. The group may be a terminal group or a bridging group.

"Alkylsulfonyl" refers to a —S(O)$_2$-alkyl group in which alkyl is as defined above. The alkyl group may be a $C_1$-$C_6$ alkyl group. Examples include, but not limited to methylsulfonyl and ethylsulfonyl. The group may be a terminal group or a bridging group.

"Alkynyl" as a group or part of a group means an aliphatic hydrocarbon group containing a carbon-carbon triple bond and which may be straight or branched and may have from 2-14 carbon atoms, 2-12 carbon atoms, or 2-6 carbon atoms in the normal chain. Exemplary structures include, but are not limited to, ethynyl and propynyl. The group may be a terminal group or a bridging group.

"Alkylaminocarbonyl" refers to an alkylamino-carbonyl group in which alkylamino is as defined above. The group may be a terminal group or a bridging group.

"Cycloalkyl" refers to a saturated or partially saturated, monocyclic or fused or spiro polycyclic, carbocycle that may contain from 3 to 9 carbons per ring, such as cyclopropyl, cyclobutyl, cyclopentyl, cyclohexyl and the like, unless otherwise specified. It includes monocyclic systems such as cyclopropyl and cyclohexyl, bicyclic systems such as decalin, and polycyclic systems such as adamantane. The group may be a terminal group or a bridging group.

"Cycloalkenyl" means a non-aromatic monocyclic or multicyclic ring system containing at least one carbon-carbon double bond and may have from 5-10 carbon atoms per ring. Exemplary monocyclic cycloalkenyl rings include cyclopentenyl, cyclohexenyl or cycloheptenyl. The cycloalkenyl group may be substituted by one or more substituent groups. The group may be a terminal group or a bridging group.

The above discussion of alkyl and cycloalkyl substituents also applies to the alkyl portions of other substituents, such as without limitation, alkoxy, alkyl amines, alkyl ketones, arylalkyl, heteroarylalkyl, alkylsulfonyl and alkyl ester substituents and the like.

"Cycloalkylalkyl" means a cycloalkyl-alkyl-group in which the cycloalkyl and alkyl moieties are as previously described. Exemplary monocycloalkylalkyl groups include cyclopropylmethyl, cyclopentylmethyl, cyclohexylmethyl and cycloheptylmethyl. The group may be a terminal group or a bridging group.

"Halogen" represents fluorine, chlorine, bromine or iodine.

"Heterocycloalkyl" refers to a saturated or partially saturated monocyclic, bicyclic, or polycyclic ring containing at least one heteroatom selected from nitrogen, sulfur, oxygen. The heterocycloalkyl group may have from 1 to 3 heteroatoms in at least one ring. Each ring may be from 3 to 10 membered, such as 4 to 7 membered. Examples of suitable heterocycloalkyl substituents include pyrrolidyl, tetrahydrofuryl, tetrahydrothiofuranyl, piperidyl, piperazyl, tetrahydropyranyl, morphilino, 1,3-diazapane, 1,4-diazapane, 1,4-oxazepane, and 1,4-oxathiapane. The group may be a terminal group or a bridging group.

"Heterocycloalkenyl" refers to a heterocycloalkyl as described above but containing at least one double bond. The group may be a terminal group or a bridging group.

"Heterocycloalkylalkyl" refers to a heterocycloalkyl-alkyl group in which the heterocycloalkyl and alkyl moieties are as previously described. Exemplary heterocycloalkylalkyl groups include (2-tetrahydrofuryl)methyl, (2-tetrahydrothiofuranyl)methyl. The group may be a terminal group or a bridging group.

"Heteroalkyl" refers to a straight- or branched-chain alkyl group that may have from 2 to 14 carbons, such as 2 to 10 carbons in the chain, one or more of which has been replaced by a heteroatom selected from S, O, P and N. Exemplary heteroalkyls include alkyl ethers, secondary and tertiary alkyl amines, amides, alkyl sulfides, and the like. The group may be a terminal group or a bridging group. As used herein reference to the normal chain when used in the context of a bridging group refers to the direct chain of atoms linking the two terminal positions of the bridging group.

"Aryl" as a group or part of a group denotes (i) an optionally substituted monocyclic, or fused polycyclic, aromatic carbocycle (ring structure having ring atoms that are all carbon) that may have from 5 to 12 atoms per ring. Examples of aryl groups include phenyl, naphthyl, and the like; (ii) an optionally substituted partially saturated bicyclic aromatic carbocyclic moiety in which a phenyl and a $C_{5-7}$ cycloalkyl or $C_{5-7}$ cycloalkenyl group are fused together to form a cyclic structure, such as tetrahydronaphthyl, indenyl or indanyl. The group may be a terminal group or a bridging group.

"Arylalkenyl" means an aryl-alkenyl-group in which the aryl and alkenyl are as previously described. Exemplary arylalkenyl groups include phenylallyl. The group may be a terminal group or a bridging group.

"Arylalkyl" means an aryl-alkyl-group in which the aryl and alkyl moieties are as previously described. Preferred arylalkyl groups contain a $C_{1-5}$ alkyl moiety. Exemplary arylalkyl groups include benzyl, phenethyl and naphthelenemethyl. The group may be a terminal group or a bridging group.

"Heteroaryl" either alone or as part of a group refers to groups containing an aromatic ring (such as a 5 or 6 membered aromatic ring) having one or more heteroatoms as ring atoms in the aromatic ring with the remainder of the ring atoms being carbon atoms. Suitable heteroatoms include nitrogen, oxygen and sulphur. Examples of heteroaryl include thiophene, benzothiophene, benzofuran, benzimidazole, benzoxazole, benzothiazole, benzisothiazole, naphtho[2,3-b] thiophene, furan, isoindolizine, xantholene, phenoxatine, pyrrole, imidazole, pyrazole, pyridine, pyrazine, pyrimidine, pyridazine, indole, isoindole, 1H-indazole, purine, quinoline, isoquinoline, phthalazine, naphthyridine, quinoxaline, cinnoline, carbazole, phenanthridine, acridine, phenazine, thiazole, isothiazole, phenothiazine, oxazole, isooxazole, furazane, phenoxazine, 2-, 3- or 4-pyridyl, 2-, 3-, 4-, 5-, or 8-quinolyl, 1-, 3-, 4-, or 5-isoquinolinyl 1-, 2-, or 3-indolyl, and 2-, or 3-thienyl. The group may be a terminal group or a bridging group.

"Heteroarylalkyl" means a heteroaryl-alkyl group in which the heteroaryl and alkyl moieties are as previously described. The heteroarylalkyl groups may contain a lower alkyl moiety. Exemplary heteroarylalkyl groups include pyridylmethyl. The group may be a terminal group or a bridging group.

"Lower alkyl" as a group means, unless otherwise specified, an aliphatic hydrocarbon group which may be straight or branched having 1 to 6 carbon atoms in the chain, for example 1 to 4 carbons such as methyl, ethyl, propyl (n-propyl or isopropyl) or butyl (n-butyl, isobutyl or tertiary-butyl). The group may be a terminal group or a bridging group.

As would be understood by the skilled person, throughout the synthesis of the compounds of Formula (I) it may be necessary to employ a protecting group on the amino group and/or on the carboxyl group in order to reversibly preserve a reactive amino or carboxyl functionality while reacting other functional groups on the compound. In such a case, the free amino group and/or the free carboxyl groups of the compounds of Formula (I) can be liberated either by deprotection of the amino group followed by deprotection of the acid moieties or vice versa.

Examples of suitable amino protecting groups that may be used include formyl, trityl, phthalimido, trichloroacetyl, chloroacetyl, bromoacetyl, iodoacetyl, and urethane-type blocking groups such as benzyloxycarbonyl ('CBZ'), 4-phenylbenzyloxycarbonyl, 2-methylbenzyloxycarbonyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4cyanobenzyloxycarbonyl, t-butoxycarbonyl ('tBoc'), 2-(4-xenyl)-isopropoxycarbonyl, 1,1-diphenyleth-1-yloxycarbonyl, 1,1-diphenylprop-1-yloxycarbonyl, 2-phenylprop-2-yloxycarbonyl, 2-(p-toluoyl)-prop-2-yloxycarbonyl, cyclopentanyloxy-carbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluoylsulfono)-ethoxycarbonyl, 2-(methylsu lfono)ethoxycarbonyl, 2-(triphenylphosphino)-ethoxycarbonyl, fluorenylmethoxycarbonyl ("FMOC"), 2-(trimethylsilyl)ethoxycarbonyl, allyloxycarbonyl, 1-(trimethylsilylmethyl)prop-1-enyloxycarbonyl, 5-benzisoxalyl-methoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decycloxy)benzyloxycarbonyl, isobornyloxycarbonyl, 1-piperidyloxycarbonlyl and the like; benzoylmethylsulfono group, 2-nitrophenylsulfenyl, diphenylphosphine oxide, and the like. The actual amino protecting group employed is not critical so long as the derivatised amino group is stable to the condition of subsequent reaction(s) and can be selectively removed as required without substantially disrupting the remainder of the molecule including any other amino protecting group(s). Preferred amino-protecting groups are t-butoxycarbonyl (Boc), and benzyloxycarbonyl (Cbz). Further examples of these groups are found in: Greene, T. W. and Wuts, P. G. M., Protective Groups in Organic Synthesis, Second edition; Wiley-Interscience: 1991; Chapter 7; McOmie, J. F. W. (ed.), Protective Groups in Organic Chemistry, Plenum Press, 1973; and Kocienski, P. J., Protecting Groups, Second Edition, Theime Medical Pub., 2000.

Examples of carboxyl protecting groups that may be used include methyl, ethyl, n-propyl, i-propyl, p-nitrobenzyl, p-methyl benzyl, p-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2'4,4'-tetramethoxybenzhydryl, t-butyl, t-amyl, trityl, 4-methoxytrityl, 4,4'-dimethoxytrityl, 4,4,'4"-trimethoxytrityl, 2-phenylprop-2-yl, trimethylsilyl, t-butyldimethylsilyl, phenacyl, 2,2,2-trichloroethyl, β-(di(n-butyl)methylsilyl)ethyl, p-toluenesulfonoethyl, 4-nitrobenzylsulfonoethyl, allyl, cinnamyl, 1-(trimethylsilylmethyl)prop-1-en-3-yl, and the like. Preferred carboxyl protecting groups are methyl and t-butyl. Further examples of these groups are found in: Greene, T. W. and Wuts, P. G. M., Protective Groups in Organic Synthesis, Second edition; Wiley-Interscience: 1991; McOmie, J. F. W. (ed.), Protective Groups in Organic Chemistry, Plenum Press, 1973; and Kocienski, P. J., Protecting Groups, Second Edition, Theime Medical Pub., 2000.

It is understood that included in the family of compounds of Formula (I) are isomeric forms including diastereoisomers, enantiomers, tautomers, and geometrical isomers in "E" or "Z" configurational isomer or a mixture of E and Z isomers. It is also understood that some isomeric forms such as diastereomers, enantiomers, and geometrical isomers can be separated by physical and/or chemical methods and by those skilled in the art.

Some of the compounds of the disclosed embodiments may exist as single stereoisomers, racemates, and/or mixtures of enantiomers and/or diastereomers. All such single stereoisomers, racemates and mixtures thereof, are intended to be within the scope of the subject matter described and claimed.

Additionally, formulae (I), (II), (III), (IV) and (V) are intended to cover, where applicable, solvated as well as unsolvated forms of the compounds. Thus, each formula includes compounds having the indicated structure, including the hydrated as well as the non-hydrated forms.

In addition to compounds of the formulae (I), (II), (III), (IV) and (V), the compounds of the various embodiments include pharmaceutically acceptable salts, prodrugs, N-oxides and active metabolites of such compounds, and pharmaceutically acceptable salts of such metabolites.

The term "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. Examples of such inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. Suitable pharmaceutically acceptable base addition salts of compounds of Formula (I) include metallic salts made from lithium, sodium, potassium, magnesium, calcium, aluminium, and zinc, and organic salts made from organic bases such as choline, diethanolamine, morpholine. Other examples of organic salts are: ammonium salts, quaternary salts such as tetramethylammonium salt; amino acid addition salts such as salts with glycine and arginine. Additional information on pharmaceutically acceptable salts can be found in Remington's Pharmaceutical Sciences, 19th Edition, Mack Publishing Co., Easton, Pa. 1995. In the case of agents that are solids, it is understood by those skilled in the art that the inventive compounds, agents and salts may exist in different crystalline or polymorphic forms, all of which are intended to be within the scope of the present invention and specified formulae.

"Prodrug" means a compound which is convertible in vivo by metabolic means (e.g. by hydrolysis, reduction or oxidation) to a compound of formula (I). For example an ester prodrug of a compound of formula (I) containing a hydroxyl group may be convertible by hydrolysis in vivo to the parent molecule. Suitable esters of compounds of formula (I) containing a hydroxyl group, are for example acetates, citrates, lactates, tartrates, malonates, oxalates, salicylates, propionates, succinates, fumarates, maleates, methylene-bis-β-hydroxynaphthoates, gestisates, isethionates, di-p-toluoyltartrates, methanesulphonates, ethanesulphonates, benzenesulphonates, p-toluenesulphonates, cyclohexylsulphamates and quinates. As another example an ester prodrug of a compound of formula (I) containing a carboxy group may be convertible by hydrolysis in vivo to the parent molecule. (Examples of ester prodrugs are those described by F. J. Leinweber, Drug Metab. Res., 18:379, 1987).

The term "pharmaceutically acceptable" refers generally to a substance or composition that is compatible chemically and/or toxicologically with the other ingredients including a formulation, and/or the subject being treated.

The term "compounds of the present invention" (unless specifically identified otherwise) refers generally to compounds, prodrugs thereof, pharmaceutically acceptable salts of the compounds and/or prodrugs, and hydrates or solvates of the compounds, salts, and/or prodrugs, as well as all stereoisomers (including diastereoisomers and enantiomers), tautomers and isotopically labelled compounds. The compounds of the present invention may exist in unsolvated as well as solvated forms with pharmaceutically acceptable solvents such as water, ethanol, and the like, and it is intended that the invention embrace both solvated and unsolvated forms.

The term "derivative thereof" when used in reference to compounds of the present invention refers generally to prodrugs, pharmaceutically acceptable salts of the compounds and/or prodrugs, and hydrates or solvates of the compounds, salts, and/or prodrugs.

Compounds of the present invention are of Formula (I)

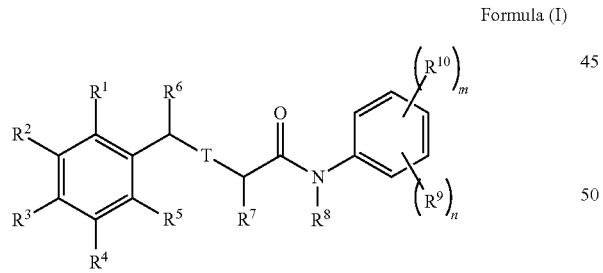

Formula (I)

wherein T, $R^1$, $R^2$, $R^3$, $R^4$, $R^5$, $R^6$, $R^7$, $R^8$, $R^9$, $R^{10}$, $R^{11}$, $R^{12}$, $R^{13}$, m, and n are as previously defined. At least one of the groups $R^1$, $R^2$, $R^3$, $R^4$ or $R^5$ contains a halogen atom.

In some embodiments, one or more of $R^1$, $R^2$, $R^3$, $R^4$, and $R^5$ is a fluoroalkoxy group. Examples of fluoro-substituted $C_{1-4}$ alkoxy groups include 1,1,1,3,3,3-hexafluoro-2-propoxy, 2-trifluoromethyl-2-propoxy, 1,1,1-trifluoro-2-propoxy, perfluoro-tert-butoxy, 2,2,3,3,4,4,4-heptafluoro-1-butoxy, 4,4,4-trifluoro-1-butoxy, 2,2,3,3,3-pentafluoropropoxy, perfluoroethoxy, 1,2,2-trifluoroethoxy, 1,1,2,2-tetrafluoroethoxy, 2,2,2-trifluoroethoxy, monofluoromethoxy, trifluoromethoxy, and difluoromethoxy. In specific embodiments, at least one of $R^1$, $R^2$, $R^3$, $R^4$, and $R^5$ is a difluoromethoxy group.

Specific compounds of the invention include compounds of any one of Formulae (III), (IV) or (V)

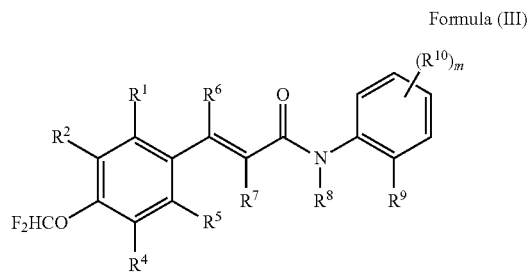

Formula (III)

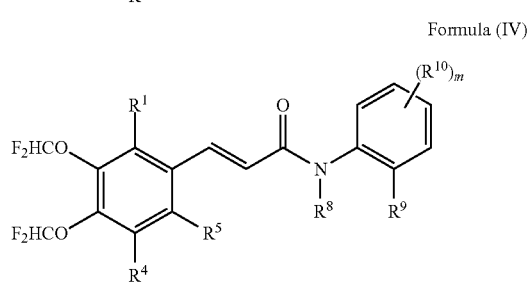

Formula (IV)

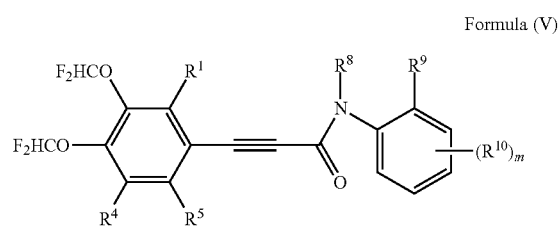

Formula (V)

Even more specific compounds of the invention include the following:

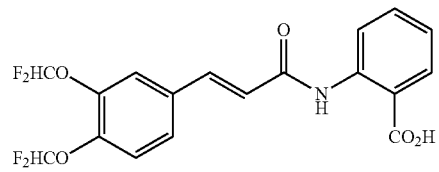

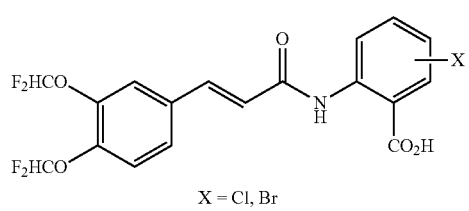

X = Cl, Br

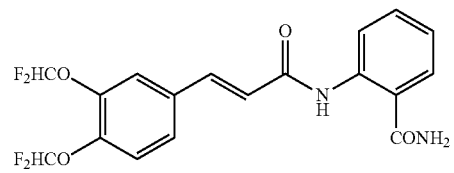

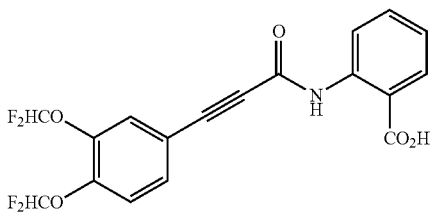
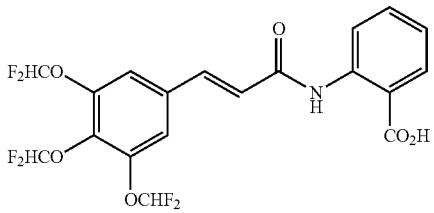
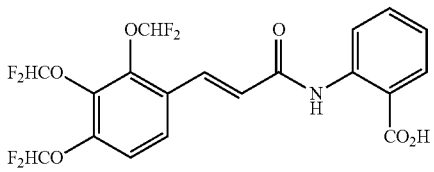
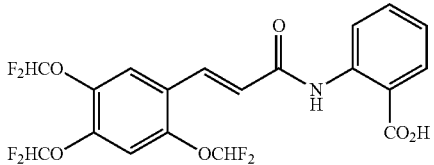
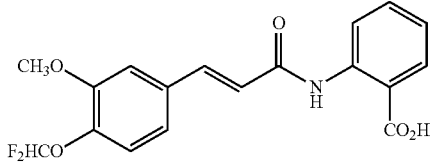
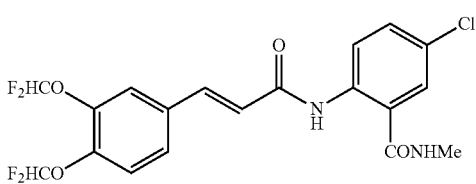
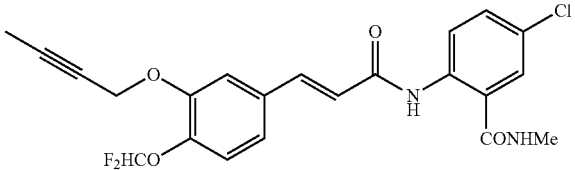
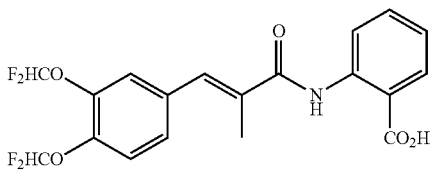

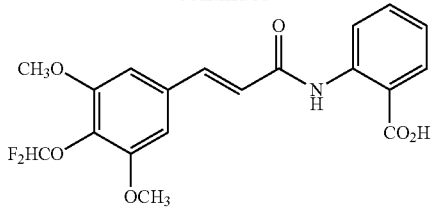
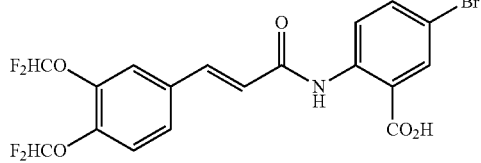
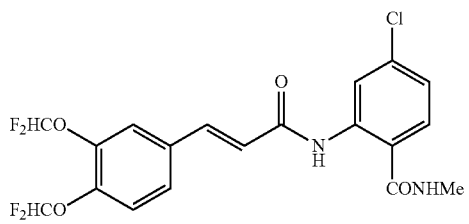
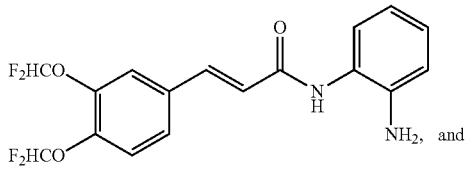
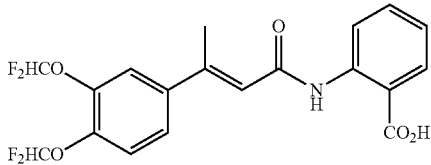

or a pharmaceutically acceptable salt or prodrug thereof.

It will be evident from the foregoing description that compounds of the present invention are analogues of tranilast. As such, the compounds of the invention may have therapeutic uses and/or be used diagnostically or for screening purposes.

The compounds of the present invention may be prepared using the reaction routes and synthesis schemes as described below, employing the techniques available in the art using starting materials that are commercially available or can be synthesised using known procedures or adaptations thereof. Whilst the preparation of particular compounds is outlined below, the skilled person will also recognize that the chemical reactions described may be readily adapted to prepare a number of other agents of the various embodiments. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Alternatively, other reactions disclosed herein or known in the art will be recognized as having applicability for preparing other compounds of the various embodiments.

Reagents useful for synthesizing compounds may be obtained or prepared according to techniques known in the art.

A synthetic route that may be suitable for producing compounds of Formula (I) is shown in Scheme 1. In this route, a substituted cinnamoyl benzamide (1) is prepared via a piperidine-catalyzed Knoevenagel condensation of an appropriately substituted carboxyacetamidobenzoic acid derivative (2) and an appropriately substituted benzaldehyde derivative (3).

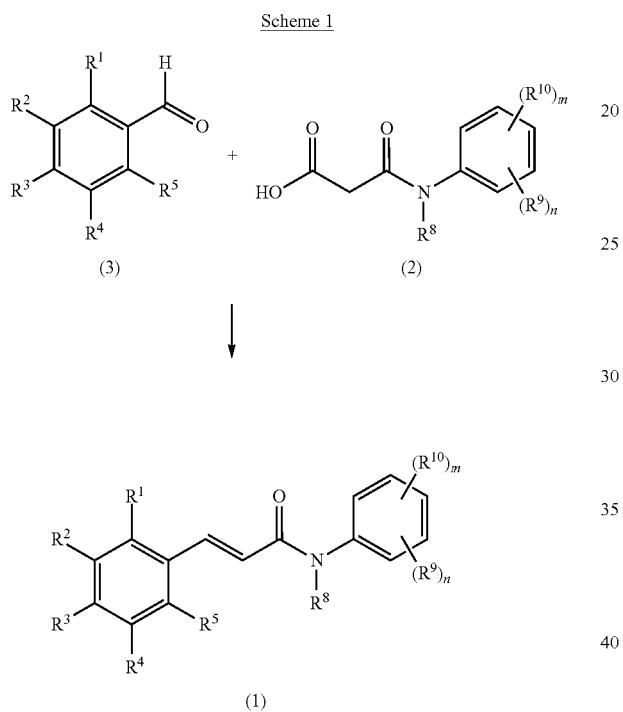

The benzaldehyde precursor (3) required for the above reaction can either be obtained from commercial sources, or can be synthesized by alkylation of precursor phenolic benzaldehydes with appropriate alkyl halides, haloalkyl tosylates (derived in turn from the corresponding alcohols), haloacetate esters or salts, or chlorodifluoromethyl sulfones. For example, the alkylation may be carried out using $CHF_2X$ (X=I, Br, Cl, OTs, etc), $ClF_2SO_2Ph$ or $ClF_2CC(O)OMe$. The alkylation reactions can be performed using a suitable base, such as potassium carbonate, in a suitable solvent, such as acetone or DMF.

Carboxyacetamidobenzoic acid derivatives (2) can be obtained by the condensation of anthranilic acid derivatives with Meldrum's acid.

Another synthetic route that may be suitable for producing compounds of Formula (I) is shown in Scheme 2. In this route, a substituted cinnamic acid (3) is converted to the corresponding acid chloride (4) (or acid bromide) which then reacts with an aminobenzamide derivative or an orthophenylenediamine derivative (5).

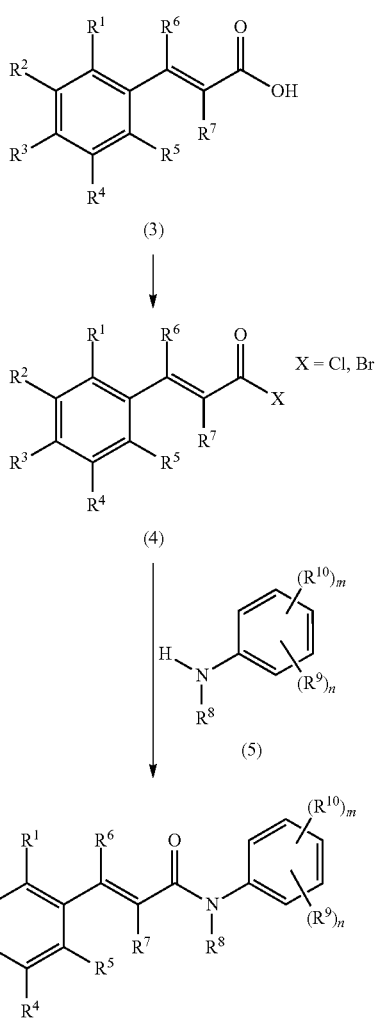

Cinnamic acid derivatives (3) can be prepared by Knoevenagel condensation of benzaldehydes with malonic acid. Aminobenzamide derivatives (5) can be synthesized by the reaction of primary amines with isatoic anhydride.

To produce compounds of Formula (I) in which T is a single bond the cinnamoyl benzamide (1) can be reduced by hydrogenation with a suitable catalyst, such as palladium on carbon, $RhCl(PPh_3)_3$, or by any other methods known in the art (see J. March, *Advanced Organic Chemistry*, John Wiley & Sons, New York 1985, pp. 694).

The compounds of Formula (I) and intermediates in their synthesis can be isolated from a reaction mixture using standard work-up and purification procedures. Suitable procedures include solvent extraction, chromatography (thin or thick layer chromatography, HPLC, flash chromatography, MPLC, etc.), recrystallisation etc.

The present invention includes salts of the compounds of Formula (I). The salts may serve as intermediates in the purification of compounds or in the preparation of other, for example pharmaceutically acceptable, acid addition salts, or they may be useful for identification, characterisation or purification. The salts can exist in conjunction with the acidic or basic portion of the molecule and can exist as acid addition, primary, secondary, tertiary, or quaternary ammonium, alkali metal, or alkaline earth metal salts. Generally, acid addition salts are prepared by the reaction of an acid with a compound of Formula (I). The alkali metal and alkaline earth metal salts are generally prepared by the reaction of the hydroxide form of the desired metal salt with a compound of Formula (I).

Acid addition salts are preferably the pharmaceutically acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicyclic, o-acetoxybenzoic, or organic sulphonic, 2-hydroxyethane sulphonic, toluene-p-sulphonic, or naphthalene-2-sulphonic acid.

The present invention also includes esters of the compounds of Formula (I), such esters being for example aliphatic esters such as alkyl esters. The esters of the compounds of Formula (I) may be pharmaceutically acceptable metabolically labile esters. These are ester derivatives of compounds of Formula (I) that are hydrolysed in vivo to afford the compound of Formula (I) and a pharmaceutically acceptable alcohol. Examples of metabolically labile esters include esters formed with alkanols in which the alkanol moiety may be optionally substituted by an alkoxy group, for example methanol, ethanol, propanol and methoxyethanol.

The compounds of the various embodiments may be prepared using the reaction routes and synthesis schemes as described above, employing the techniques available in the art using starting materials that are readily available. The person skilled in the art will recognise that the chemical reactions described may be readily adapted to prepare a number of other compounds. For example, the synthesis of non-exemplified compounds may be successfully performed by modifications apparent to those skilled in the art, e.g. by appropriately protecting interfering groups, by changing to other suitable reagents known in the art, or by making routine modifications of reaction conditions. A list of suitable protecting groups in organic synthesis can be found in T. W. Greene's Protective Groups in Organic Synthesis, 3$^{rd}$ Edition, John Wiley & Sons, 1991. Reagents useful for synthesizing compounds may be obtained or prepared according to techniques known in the art.

The utility of compounds of Formula (I) can be tested using any of the following methods:
  (i) In a renal cell line by measuring proline incorporation after transforming growth factor-β stimulation;
  (ii) Matrix synthesis may be stimulated by platelet derived growth factor (PDGF). Accordingly, mesangial cells incubated with PDGF can be used to demonstrate proline incorporation, which is an indicator of matrix synthesis and thereby a model for fibrosis; or
  (iii) Matrix synthesis may be stimulated by both angiotensin II or transforming growth factor beta (TGF-β). Accordingly, neonatal cardiac fibroblasts incubated with angiotensin II or TGF-β can be used to demonstrate proline incorporation, which is an indicator of matrix synthesis and thereby a model for fibrosis.

Examples of materials and methods for use with the compounds of the present invention will now be provided. In providing these examples, it is to be understood that the specific nature of the following description is not to limit the generality of the above description.

EXAMPLES

Experimental

Electrospray ionization (ESI) high resolution mass spectra (HRMS) were obtained on a Finnigan hybrid LTQ-FT mass spectrometer (Thermo Electron Corp.). Proton nuclear magnetic resonance ($^1$H NMR) and proton decoupled carbon nuclear magnetic resonance ($^{13}$C NMR) spectra were obtained on Unity 400, Innova 400 or Innova 500 instruments (Melbourne, Australia) operating at 400 or 500 MHz for $^1$H and at 100 or 125 MHz for $^{13}$C. All signals were referenced to solvent peaks (CDCl$_3$: 7.26 ppm for $^1$H and 77.0 ppm for $^{13}$C; DMSO-d$_6$: 2.49 ppm for $^1$H and 39.5 ppm for $^{13}$C). Infrared (IR) spectra were obtained using a PerkinElmer Spectrum One FT-IR spectrometer with zinc selenide/diamond Universal ATR Sampling Accessory. Melting points were obtained using a Reichert-Jung hot stage apparatus and are corrected. Analytical thin layer chromatography (TLC) was conducted on 2 mm thick silica gel GF$_{254}$. Compounds were visualised with solutions of 20% w/w phosphomolybdic acid in ethanol, 20% w/w potassium permanganate in water or under UV (365 nm). Flash chromatography was performed according to the method of Still et al.[1] with Merck Silica Gel 60. Petrol refers to the fraction boiling at 40-60° C. All other reagents were used as received.

Example 1

Synthesis of Compounds of Formula (I)

2-[(Carboxyacetyl)amino]benzoic acid

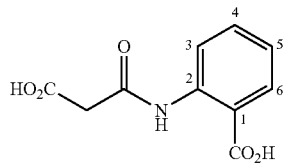

Anthranilic acid (300 g, 2.08 mol) was added to a solution of Meldrum's acid (272 g, 1.98 mol) in toluene (2.0 L). The reaction flask was fitted with a Dean-Stark apparatus and the suspension was heated to reflux for 3 h. The suspension was cooled, filtered, washed with toluene and dried. 2-[(Carboxyacetyl)amino]benzoic acid (381 g, 86%) was obtained as a colourless solid; mp 171-173° C.; δ$_H$ (500 MHz, DMSO-d$_6$) 3.45 (br s, 2H, CH$_2$), 7.16 (t, J$_{3,4}$=J$_{4,5}$=8.0 Hz, 1H, H4), 7.59 (td, J$_{4,5}$=J$_{5,6}$=8.0, J$_{3,5}$=1.5 Hz, 1H, H5), 7.97 (dd, J$_{3,4}$=8.0, J$_{3,5}$=1.5 Hz, 1H, H3), 8.44 (d, J$_{5,6}$=8.0 Hz, 1H, H6), 11.27 (s, 1H, NH), 12.83 (br s, 1H, CO$_2$H), 13.57 (br s, 1H, CO$_2$H); δ$_C$ (125 MHz, DMSO-d$_6$) 45.0, 117.0, 120.3, 123.1, 131.2, 134.1, 140.4, 164.9, 169.1, 169.3; ν$_{max}$ 760, 1234, 1385, 1544, 1684, 1712, 2653, 2964, 3119 cm$^{-1}$.

3,4-Bis(difluoromethoxy)benzaldehyde & 4-difluoromethoxy-3-hydroxybenzaldehyde

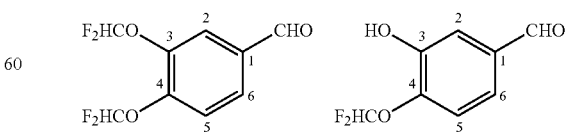

Methyl chlorodifluoroacetate (15.3 mL, 145 mmol) was added to a suspension of 3,4-dihydroxybenzaldehyde (5.0 g, 36 mmol) and potassium carbonate (20.0 g, 145 mmol) in DMF (10 mL). The suspension was heated to 60° C. for 16 h and then diluted with water. The aqueous phase was extracted with EtOAc and the combined organic fractions were washed with saturated aqueous NaHCO$_3$, water, brine, dried and concentrated. The residue was purified by column chromatography, eluting with 10% EtOAc/petrol to give 3,4-bis(difluoromethoxy)benzaldehyde (1.1 g, 13%) as a colourless oil; $\delta_H$ (400 MHz, CDCl$_3$) 6.60 (t, J=72 Hz, 1H, OCHF$_2$), 6.64 (t, J=72 Hz, 1H, OCHF$_2$), 7.42 (d, J$_{5,6}$=8.0 Hz, 1H, H5), 7.76-7.78 (m, 2H, H2, H6), 9.96 (s, 1H, CHO); $\delta_C$ (125 MHz, CDCl$_3$) 115.2 (t, J=259 Hz), 115.4 (t, J=259 Hz), 121.5, 122.2, 128.5, 134.2, 142.4, 147.0 189.7; $\nu_{max}$ 794, 1038, 1381, 1509, 1698, cm$^{-1}$. Further elution provided 4-difluoromethoxy-3-hydroxybenzaldehyde (1.43 g, 21%) as a colourless crystalline solid; mp 94-95° C. (recrystallized from EtOAc); $\delta_H$ (500 MHz, CDCl$_3$) 5.82 (s, 1H, OH), 6.65 (t, J=72.0 Hz, 1H, CHF$_2$), 7.27 (d, J$_{5,6}$=8.0 Hz, 1H, H5), 7.44 (dd, J$_{5,6}$=8.0, J$_{2,6}$=2.0 Hz, 1H, H6), 7.54 (d, J$_{2,6}$=2.0 Hz, 1H, H2), 9.92 (s, 1H, CHO); $\delta_C$ (125 MHz, CDCl$_3$) 115.6 (t, J=259 Hz), 117.1, 119.2, 123.1, 134.6, 142.9, 147.8, 190.9; $\nu_{max}$ 1087, 1237, 1508, 1592, 1686, 2859, 3313 cm$^{-1}$.

(E)-2-[[3,4-Bis(difluoromethoxy)phenyl)-1-oxo-2-propenyl]amino]benzoic acid

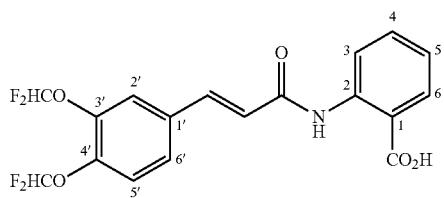

Piperidine (100 μL, 1.01 mmol) was added to a suspension of 3,4-bis(difluoromethoxy)benzaldehyde (240 mg, 1.01 mmol) and 2-[(carboxyacetyl)amino]benzoic acid (204 mg, 0.92 mmol) in toluene (5.0 mL). The reaction flask was fitted with a Dean-Stark apparatus and heated to reflux for 30 min. The reaction was then cooled to rt and the resulting suspension was filtered and washed with toluene. The piperidinium salt was dissolved in MeOH (5 mL) and water (2 mL) and the solution was acidified with 50% aqueous AcOH. The crude product was collected by filtration and recrystallised from EtOH/water, filtered and washed with water to afford (E)-2-[[3,4-bis(difluoromethoxy)phenyl)-1-oxo-2-propenyl]amino]benzoic acid (259 mg, 71%) as a colourless crystalline solid; mp 190-193° C.; $\delta_H$ (400 MHz, DMSO-d$_6$) 6.96 (d, J=15.6 Hz, 1H, CH=CHCO), 7.18 (t, J$_{3,4}$=J$_{4,5}$=8.0 Hz, 1H, H4), 7.27 (t, J=73 Hz, 1H, OCHF$_2$), 7.38 (d, J$_{5',6'}$=8.0 Hz, 1H, H5'), 7.61 (d, J=15.6 Hz, 1H, CH=CHCO), 7.62 (t, J$_{4,5}$=J$_{5,6}$=8.0 Hz, 1H, H5), 7.78 (d, J$_{2',6'}$=1.6 Hz, 1H, H2'), 7.68 (dd, J$_{5',6'}$=8.0, J$_{2',6'}$=1.6 Hz, 1H, H6'), 8.00 (d, J$_{3,4}$=8.0 Hz, 1H, H3), 8.69 (d, J$_{5,6}$=8.0 Hz, 1H, H6), 11.35 (s, 1H, NH), 13.56 (br s, 1H, CO$_2$H); $\delta_C$ (100 MHz, DMSO-d$_6$) 116.3 (t, J=258 Hz), 116.5 (t, J=258 Hz), 117.0, 120.1, 120.5, 120.8, 123.0, 123.8, 126.7, 131.1, 132.8, 133.9, 139.3, 140.7, 141.9, 142.7, 163.5, 169.4; HRMS (ESI$^-$) calculated for C$_{18}$H$_{13}$F$_4$NO$_5$ [M-H]$^-$ 398.0646, found 398.0652; $\nu_{max}$ 1034, 1217, 1513, 1604, 1683, 2892, 3466 cm$^{-1}$.

5-Bromo-2-[(carboxyacetyl)amino]benzoic acid

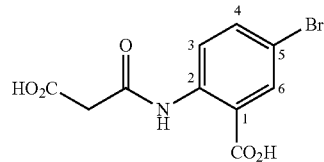

5-Bromoanthranilic acid (0.30 g, 1.4 mmol) was added to a solution of Meldrum's acid (0.24 g, 1.7 mmol) in toluene (5.0 mL). The reaction flask was fitted with a Dean-Stark apparatus and the suspension was heated to reflux for 3 h. The suspension was cooled, filtered, washed with toluene and dried. Crude 5-bromo-2-[(carboxyacetyl)amino]benzoic acid (0.34 g, 81%) was obtained as a colourless solid; mp 203-206° C.; $\delta_H$ (500 MHz, DMSO-d$_6$) 3.48 (s, 2H, CH$_2$), 7.78 (d, J$_{3,4}$=8.4 Hz, 1H, H4), 8.04 (s, 1H, H6), 8.40 (d, J$_{3,4}$=8.4 Hz, 1H, H3), 11.20 (s, 1H, NH), 12.80 (br s, 1H, CO$_2$H); $\delta_C$ (125 MHz, DMSO-d$_6$) 44.7, 114.5, 119.4, 122.5, 133.1, 136.4, 139.4, 164.7, 167.8, 168.9; $\nu_{max}$ 1224, 1373, 1520, 1683, 2985 cm$^{-1}$.

(E)-2-[[3,4-Bis(difluoromethoxy)phenyl)-1-oxo-2-propenyl]amino]-5-bromobenzoic acid

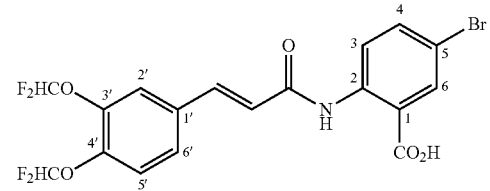

Piperidine (100 μL, 1.01 mmol) was added to a suspension of 3,4-bis(difluoromethoxy)benzaldehyde (240 mg, 1.01 mmol) and 2-[(carboxyacetyl)amino]-5-bromobenzoic acid (277 mg, 0.92 mmol) in toluene (5.0 mL). The reaction flask was fitted with a Dean-Stark apparatus and heated to reflux for 30 min. The reaction was then cooled to rt and the resulting suspension was filtered and washed with toluene. The piperidinium salt was dissolved in MeOH (5 mL) and water (2 mL) and the solution was acidified with 50% aqueous AcOH. The crude product was collected by filtration and recrystallised from EtOH/water and filtered to afford (E)-2-[[3,4-bis(difluoromethoxy)phenyl)-1-oxo-2-propenyl]amino]-5-bromobenzoic acid (198 mg, 45%) as a colourless crystalline solid; mp 223-226° C.; $\delta_H$ (400 MHz, DMSO-d$_6$) 6.96 (d, J=15.6 Hz, 1H, CH=CHCO), 7.26 (t, J=73 Hz, 1H, OCHF$_2$), 7.27 (t, J=73 Hz, 1H, OCHF$_2$), 7.38 (d, J$_{5',6'}$=8.0 Hz, 1H, H5'), 7.61 (d, J=15.6 Hz, 1H, CH=CHCO), 7.68 (dd, J$_{5',6'}$=8.0, J$_{2',6'}$=1.6 Hz, 1H, H6'), 7.78 (d, J$_{2',6'}$=1.6 Hz, 1H, H2'), 7.80 (dd, J$_{3,4}$=9.2, J$_{4,6}$=2.8 Hz, 1H, H4), 8.08 (d, J$_{4,6}$=2.8 Hz, 1H, H6), 8.55 (d, J$_{3,4}$=9.2 Hz, 1H, H3), 11.28 (s, 1H, NH); $\delta_C$ (100 MHz, DMSO-d$_6$) 116.3 (t, J=259 Hz), 116.5 (t, J=259 Hz), 116.5, 119.3, 120.1, 120.8, 122.6, 123.5, 126.7, 132.7, 133.2, 136.4, 139.7, 139.8, 141.9, 142.8, 163.6, 168.0; HRMS (ESI) calculated for $C_{18}H_{12}BrF_4NO_5$ [M-H]⁻ 475.9751, found 475.9752; $v_{max}$ 1102, 1152, 1509, 1595, 1673, 1694, 3128 cm⁻¹.

4-(Difluoromethoxy)-3-methoxybenzaldehyde

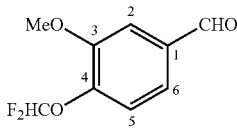

Methyl chlorodifluoroacetate (1.4 mL, 13 mmol) was added to a suspension of vanillin (1.0 g, 6.6 mmol) and potassium carbonate (2.0 g, 14 mol) in DMF (10 mL). The suspension was heated to 65-70° C. for 16 h and the suspension was diluted with water. The aqueous phase was extracted with EtOAc and the combined organic fractions were washed with saturated aqueous NaHCO₃, water, brine, dried and concentrated. The residue was purified by column chromatography, eluting with 10% EtOAc/petrol to give 4-(difluoromethoxy)-3-methoxybenzaldehyde (0.54 g, 41%) as a colourless oil; $\delta_H$ (400 MHz, CDCl₃) 3.95 (s, 3H, OCH₃), 6.60 (t, J=74 Hz, 1H, OCHF₂), 7.30 (d, $J_{5,6}$=8.0 Hz, 1H, H5), 7.45 (dd, $J_{5,6}$=8.0, $J_{2,6}$=2.0 Hz, 1H, H6), 7.50 (d, $J_{2,6}$=2.0 Hz, 1H, H2), 9.93 (s, 1H, CHO); $\delta_C$ (100 MHz, CDCl₃) 56.2, 110.9, 115.5 (t, J=256 Hz), 121.5, 125.0, 134.5, 144.9, 151.5, 190.8.

(E)-2-[[3-Methoxy-4-(difluoromethoxy)phenyl]-1-oxo-2-propenyl]amino]benzoic acid

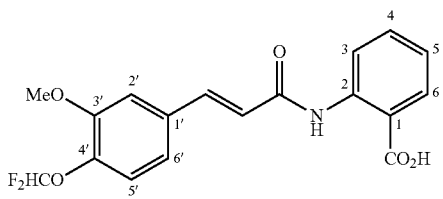 [SMILES: COc1cc(/C=C/C(=O)Nc2ccccc2C(=O)O)ccc1OC(F)F]

Piperidine (0.25 mL, 2.6 mmol) was added to a suspension of 4-(difluoromethoxy)-3-methoxybenzaldehyde (0.52 g, 2.6 mmol) and 2-[(carboxyacetyl)amino]benzoic acid (0.52 mg, 2.6 mmol) in toluene (5.0 mL). The reaction flask was fitted with a Dean-Stark apparatus and heated to reflux for 30 min. The reaction was then cooled to rt and the resulting suspension was filtered and washed with toluene. The piperidinium salt was dissolved in MeOH (5 mL) and water (2 mL) and the solution was acidified with 50% aqueous AcOH. The crude product was collected by filtration and recrystallised from EtOH/water, filtered and washed with water to afford (E)-2-[[3-methoxy-4-(difluoromethoxy)phenyl]-1-oxo-2-propenyl]amino]benzoic acid (259 mg, 71%) as a colourless crystalline solid; mp 172-174° C.; $\delta_H$ (500 MHz, DMSO-d₆) 3.90 (s, 3H, OCH₃), 6.94 (d, J=15.6 Hz, 1H, CH=CHCO), 7.12 (t, J=75 Hz, 1H, OCHF₂), 7.17 (t, $J_{3,4}$=$J_{4,5}$=8.0 Hz, 1H, H4), 7.20 (d, $J_{5',6'}$=8.0 Hz, 1H, H5'), 7.32 (dd, $J_{5',6'}$=8.0, $J_{2',6'}$=2.0 Hz, 1H, H6'), 7.56 (d, $J_{2',6'}$=2.0 Hz, 1H, H2'), 7.61 (d, J=15.6 Hz, 1H, CH=CHCO), 7.62 (dt, $J_{4,5}$=$J_{5,6}$=8.0, $J_{3,5}$=1.5 Hz, 1H, H5), 8.00 (dd, $J_{3,4}$=8.0, $J_{3,5}$=1.5 Hz, 1H, H3), 8.61 (d, $J_{5,6}$=8.0 Hz, 1H, H6), 11.33 (s, 1H, NH), 13.60 (br s, 1H, CO₂H); $\delta_C$ (125 MHz, DMSO-d₆) 56.1, 112.3, 114.5, 116.5 (t, J=256 Hz), 116.8, 120.4, 120.8, 121.4, 122.7, 122.9, 131.1, 132.9, 134.0, 140.6, 140.8, 150.7, 163.7, 169.4; HRMS (ESI⁻) calculated for $C_{18}H_{15}F_2NO_5$ [M-H]⁻ 362.0835, found 362.0839; $v_{max}$ 1032, 1260, 1586, 1604, 1661, 2988, 3509 cm⁻¹.

3-(But-2-ynyloxy)-4-difluoromethoxybenzaldehyde

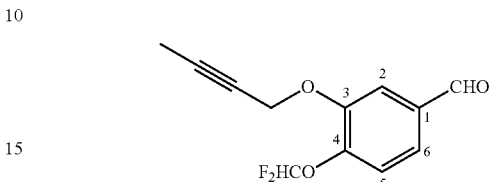

But-2-ynyl bromide (0.29 mL, 3.4 mmol) was added to a suspension of 4-difluoromethoxy-3-hydroxybenzaldehyde (0.43 g, 2.3 mmol) and potassium carbonate (0.95 g, 6.9 mmol) in acetonitrile (5 mL). The suspension was heated to reflux for 16 h and then concentrated under reduced pressure. Water was added and the aqueous phase was extracted with EtOAc. The combined organic fractions were washed with water, brine, dried. The product was concentrated under reduced pressure providing 3-(but-2-ynyloxy)-4-difluoromethoxybenzaldehyde (0.53 g, 97%) as a yellow crystalline solid; mp 46-47° C.; $\delta_H$ (500 MHz, CDCl₃) 1.86 (t, J=2.5 Hz, 3H, C≡CCH₃), 4.81 (q, J=2.5 Hz, 2H, OCH₂), 6.68 (t, J=72.0 Hz, 1H, CHF₂), 7.33 (d, $J_{5,6}$=8.0 Hz, 1H, H5), 7.50 (dd, $J_{5,6}$=8.0, $J_{2,6}$=2.0 Hz, 1H, H6), 7.63 (d, $J_{2,6}$=2.0 Hz, 1H, H2), 9.96 (s, 1H, CHO); $\delta_C$ (125 MHz, CDCl₃) 3.7, 57.5, 72.7, 85.3, 113.4, 115.6 (t, J=256 Hz), 121.8, 125.1, 134.4, 145.3, 149.7, 190.7; $v_{max}$ 1123, 1268, 1435, 1505, 1597, 1698, 2858 cm⁻¹.

(E)-3-(3-(But-2-ynyloxy)-4-difluoromethoxyphenyl)-2-propenoic acid

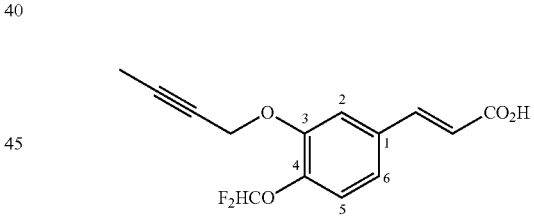

A solution of 3-(but-2-ynyloxy)-4-difluoromethoxybenzaldehyde (0.53 g, 2.2 mmol) and malonic acid (0.34 g, 3.3 mmol) in a mixture of piperidine (0.2 mL) and pyridine (5.0 mL) was heated to 120° C. and stirred for 16 h. The mixture was cooled to rt and acidified with 1 M HCl. The crude product was collected by filtration and recrystallised from acetonitrile to give (E)-3-(3-(but-2-ynyloxy)-4-difluoromethoxyphenyl)-2-propenoic acid (0.38 g, 61%) as a colourless crystalline solid; mp 206-208° C.; $\delta_H$ (500 MHz, DMSO-d₆) 1.84 (t, J=2.2 Hz, 3H, C≡CH₃), 4.87 (q, J=2.2 Hz, 2H, OCH₂), 6.55 (d, J=16.0 Hz, 1H, CH=CHCO₂H), 7.13 (t, J=72.0 Hz, 1H, CHF₂), 7.19 (d, $J_{5,6}$=8.0 Hz, 1H, H5), 7.30 (dd, $J_{5,6}$=8.0, $J_{2,6}$=2.0 Hz, 1H, H6), 7.52 (d, $J_{2,6}$=2.0 Hz, 1H, H2), 7.54 (d, J=16.0 Hz, 1H, CH=CHCO₂H), 12.41 (br s, 1H, CO₂H); $\delta_C$ (125 MHz, DMSO-d₆) 3.1, 56.8, 74.1, 84.1, 113.6, 116.4 (t, J=256 Hz), 119.7, 120.6, 122.0, 132.4, 141.2, 142.9, 148.6, 167.4; $v_{max}$ 1011, 1113, 1267, 1516, 1629, 1686, 2578, 2924 cm⁻¹.

(E)-2-[[3-(3-(But-2-ynyloxy)-4-difluoromethoxyphenyl)-1-oxo-2-propenyl]amino]-5-chloro-N-methylbenzamide

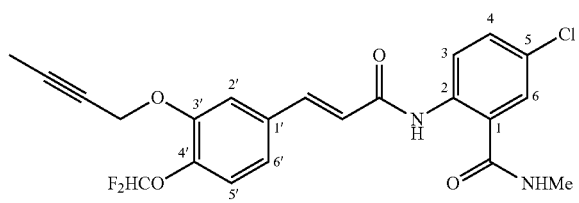

A suspension of (E)-3-(3-(but-2-ynyloxy)-4-difluoromethoxyphenyl)-2-propenoic acid (0.32 g, 1.1 mmol) in CH$_2$Cl$_2$ (5 mL) was treated with oxalyl chloride (0.38 mL, 6.8 mmol) and catalytic DMF (1 drop). The solution was stirred at rt for 2 h and the solvent was removed under reduced pressure to give the acid chloride as a yellow solid. A solution of the acid chloride (1.1 mmol) in pyridine (3.0 mL) was added to a cooled solution of 2-amino-5-chloro-N-methylbenzamide (0.47 g, 2.5 mmol) in pyridine (2.0 mL) at 0° C. The suspension was stirred at 0° C. for 1 h, warmed to rt and stirred for 16 h and then acidified with 1 M HCl. The precipitate was collected by filtration and recrystallised from acetonitrile providing (E)-2-[[3-(3-(but-2-ynyloxy)-4-methoxyphenyl)-1-oxo-2-propenyl]amino]-4-chloro-N-methylbenzamide (0.10 g, 20%) as a colourless crystalline solid; mp 172-173° C.; δ$_H$ (500 MHz, DMSO-d$_6$) 1.83 (t, J=2.5 Hz, 3H, C≡CCH$_3$), 2.77 (d, J=4.5 Hz, 3H, NHCH$_3$), 4.87 (q, J=2.5 Hz, 2H, OCH$_2$), 6.84 (d, J=16.0 Hz, 1H, CH=CHCO), 7.11 (t, J=72.0 Hz, 1H, CHF$_2$), 7.18 (d, J$_{5',6'}$=8.0 Hz, 1H, H5'), 7.31 (dd, J$_{3,4}$=8.0, J$_{4,6}$=2.0 Hz, 1H, H4), 7.54-7.57 (m, 2H, H2', H6'), 7.53 (d, J=16.0 Hz, 1H, CH=CHCO), 7.77 (d, J$_{5,6}$=8.0 Hz, 1H, H6), 8.53 (d, J$_{3,5}$=2.0 Hz, 1H, H3), 8.83 (m, 1H, NHCH$_3$), 11.52 (s, 1H, NH); δ$_C$ (125 MHz, DMSO-d$_6$) 3.1, 26.3, 56.9, 74.2, 84.1, 113.7, 116.4 (t, J=256 Hz), 120.6, 122.1, 122.5, 122.6, 126.6, 127.6, 131.4, 132.5, 137.8, 140.5, 141.1, 148.6, 163.5, 167.3; HRMS (ESI$^+$) calculated for C$_{22}$H$_{19}$ClF$_2$N$_2$O$_4$ [M+Na]$^+$ 471.0894, found 471.0894; ν$_{max}$ 1122, 1260, 1505, 1596, 1620, 1662, 3294 cm$^{-1}$.

(E)-3,4-Bis(difluoromethoxy)phenyl-2-propenoic acid

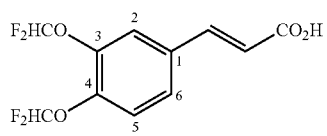

A solution of 3,4-bis(difluoromethoxy)benzaldehyde (0.41 g, 1.7 mmol) and malonic acid (0.27 g, 2.6 mmol) in a mixture of piperidine (0.2 mL) and pyridine (5.0 mL) was heated to 120° C. and stirred for 16 h. The mixture was cooled to rt and acidified with 1 M HCl. The crude product was collected by filtration and recrystallised from EtOH to give (E)-3,4-bis(difluoromethoxy)phenyl-2-propenoic acid (0.38 g, 79%) as a colourless crystalline solid; mp 152-154° C.; δ$_H$ (500 MHz, DMSO-d$_6$) 6.57 (d, J=16.0 Hz, 1H, CH=CHCO$_2$H), 7.24 (t, J=72.0 Hz, 1H, CHF$_2$), 7.25 (t, J=72.0 Hz, 1H, CHF$_2$), 7.36 (d, J$_{5,6}$=8.0 Hz, 1H, H5), 7.57 (d, J=16.0 Hz, 1H, CH=CHCO$_2$H), 7.63 (dd, J$_{5,6}$=8.0, J$_{2,6}$=2.0 Hz, 1H, H6), 7.72 (d, J$_{2,6}$=2.0 Hz, 1H, H2), 12.48 (br s, 1H, CO$_2$H); δ$_C$ (125 MHz, DMSO-d$_6$); 117.0 (t, J=256 Hz), 117.1 (t, J=256 Hz), 120.7, 121.4, 121.5, 127.2, 133.4, 142.5, 142.6, 143.5, 167.9; ν$_{max}$ 1037, 1266, 1519, 1632, 1692, 2596, 2971 cm$^{-1}$.

(E)-2-[[3,4-Bis(difluoromethoxy)phenyl)-1-oxo-2-propenyl]amino]-5-chloro-N-methylbenzamide

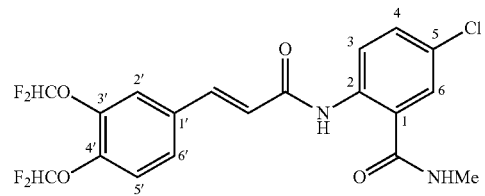

A suspension of (E)-3,4-bis(difluoromethoxy)phenyl-2-propenoic acid (0.10 g, 0.42 mmol) in CH$_2$Cl$_2$ (5 mL) was treated with oxalyl chloride (0.14 mL, 1.7 mmol) and catalytic DMF (1 drop). The solution was stirred at rt for 1 h and the solvent was removed under reduced pressure to give the acid chloride as a yellow solid. A solution of the acid chloride (0.42 mmol) in pyridine (2.0 mL) was added to a cooled solution of 2-amino-5-chloro-N-methylbenzamide (0.12 g, 0.63 mmol) in pyridine (2.0 mL) at 0° C. The suspension was stirred at 0° C. for 1 h, warmed to rt and stirred for 16 h and then acidified with 1 M HCl. The precipitate was collected by filtration and recrystallised from EtOH/water providing (E)-2-[[3,4-bis(difluoromethoxy)phenyl)-1-oxo-2-propenyl]amino]-5-chloro-N-methylbenzamide (80 mg, 43%) as a pale brown crystalline solid; mp 185.5-187.5° C.; δ$_H$ (500 MHz, DMSO-d$_6$) 2.81 (d, J=4.5 Hz, 3H, NHCH$_3$), 6.93 (d, J=15.6 Hz, 1H, CH=CHCO), 7.26 (t, J=73 Hz, 1H, OCHF$_2$), 7.27 (t, J=73 Hz, 1H, OCHF$_2$), 7.37 (d, J$_{5',6'}$=8.0 Hz, 1H, H5'), 7.57 (dd, J$_{5',6'}$=8.0, J$_{2',6'}$=1.6 Hz, 1H, H6'), 7.59 (d, J=15.6 Hz, 1H, CH=CHCO), 7.66 (dd, J$_{3,4}$=8.5, J$_{4,6}$=2.0 Hz, 1H, H4), 7.80 (m, 2H, H2', H6), 8.56 (d, J$_{3,4}$=8.5 Hz, 1H, H3), 8.85 (m, 1H, NHCH$_3$), 11.54 (s, 1H, NH); δ$_C$ (125 MHz, DMSO-d$_6$) 26.3, 116.3 (t, J=259 Hz), 116.5 (t, J=259 Hz), 119.9, 120.7, 122.5, 122.6, 123.5, 126.6, 126.7, 127.7, 131.4, 132.8, 137.7, 139.4, 141.9, 142.7, 163.3, 167.3; HRMS (ESI$^+$) calculated for C$_{19}$H$_{15}$ClF$_4$N$_2$O$_4$ [M+Na]$^+$ 469.0549, found 469.0549; ν$_{max}$ 1052, 1267, 1508, 1633, 1684, 3303 cm$^{-1}$.

(E)-2-[[3,4-Bis(difluoromethoxy)phenyl)-1-oxo-2-propenyl]amino]-4-chloro-N-methylbenzamide

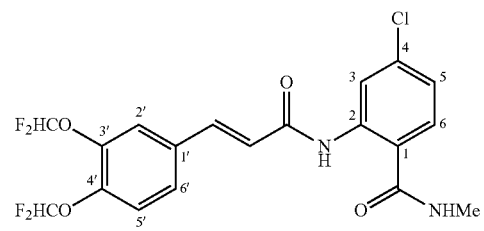 [SMILES: CNC(=O)c1ccc(Cl)cc1NC(=O)/C=C/c1ccc(OC(F)F)c(OC(F)F)c1]

A suspension of (E)-3,4-bis(difluoromethoxy)phenyl-2-propenoic acid (0.10 g, 0.42 mmol) in CH$_2$Cl$_2$ (5 mL) was treated with oxalyl chloride (0.14 mL, 1.7 mmol) and catalytic DMF (1 drop). The solution was stirred at rt for 1 h and the solvent was removed under reduced pressure to give the acid chloride as a yellow solid. A solution of the acid chloride (0.42 mmol) in pyridine (2.0 mL) was added to a cooled solution of 2-amino-4-chloro-N-methylbenzamide (0.12 g, 0.63 mmol) in pyridine (2.0 mL) at 0° C. The suspension was stirred at 0° C. for 1 h, warmed to rt and stirred for 16 h and then acidified with 1 M HCl. The precipitate was collected by filtration and recrystallised from EtOH/water providing (E)-2-[[3,4-bis(difluoromethoxy)phenyl]-1-oxo-2-propenyl] amino]-5-chloro-N-methylbenzamide (95 mg, 51%) as a pale brown crystalline solid; mp 191.5-195.5° C.; $\delta_H$ (500 MHz, DMSO-$d_6$) 2.82 (d, J=4.5 Hz, 3H, NHCH$_3$), 6.94 (d, J=15.6 Hz, 1H, CH=CHCO), 7.27 (t, J=73 Hz, 1H, OCHF$_2$), 7.28 (t, J=73 Hz, 1H, OCHF$_2$), 7.26 (dd, $J_{5,6}$=8.0, $J_{3,5}$=1.6 Hz, 1H, H5), 7.39 (d, $J_{5',6'}$=8.0 Hz, 1H, H5'), 7.59 (d, J=15.6 Hz, 1H, CH=CHCO), 7.69 (dd, $J_{5',6'}$=8.5, $J_{2',6'}$=2.5 Hz, 1H, H6'), 7.77 (d, $J_{5,6}$=2.5 Hz, 1H, H6), 7.80 (d, $J_{2',6'}$=2.5 Hz, 1H, H2'), 8.67 (d, $J_{3,5}$=2.5 Hz, 1H, H3), 8.84 (m, 1H, NHCH$_3$), 11.82 (s, 1H, NH); $\delta_C$ (125 MHz, DMSO-$d_6$) 26.3, 116.3 (t, J=259 Hz), 116.5 (t, J=259 Hz), 119.2, 119.9, 119.9, 120.7, 122.6, 123.4, 126.8, 129.6, 132.7, 136.2, 139.7, 140.2, 141.9, 142.8, 163.5, 167.8; HRMS (ESI$^+$) calculated for $C_{19}H_{15}ClF_4N_2O_4$ [M+Na]$^+$ 469.0549, found 469.0546; $v_{max}$ 1038, 1113, 1260, 1505, 1578, 1626, 3025, 3382 cm$^{-1}$.

4-(Difluoromethoxy)-3,5-dimethoxybenzaldehyde

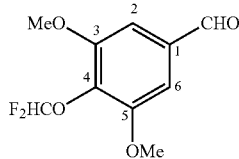

Methyl chlorodifluoroacetate (0.58 mL, 5.5 mmol) was added to a suspension of 4-hydroxy-3,4-dimethoxybenzaldehyde (0.50 g, 2.7 mmol) and potassium carbonate (0.76 g, 5.5 mol) in DMF (5.0 mL). The suspension was heated to 65-70° C. for 16 h and the suspension was diluted with water. The aqueous phase was extracted with EtOAc and the combined organic fractions were washed with saturated aqueous NaHCO$_3$, water, brine, dried and concentrated. The crude product was recrystallised from EtOAc/petrol providing 4-(difluoromethoxy)-3,5-dimethoxybenzaldehyde (0.25 g, 39%) as a colourless crystalline solid; mp 113-115° C.; $\delta_H$ (400 MHz, CDCl$_3$) 3.95 (s, 6H, OCH$_3$), 6.65 (t, J=74 Hz, 1H, OCHF$_2$), 7.15 (s, 2H, H2, H6), 9.91 (s, 1H, CHO); $\delta_C$ (100 MHz, CDCl$_3$) 56.5, 106.3, 116.2 (t, J=256 Hz), 134.1, 153.5, 190.8; $v_{max}$ 831, 1048, 1099, 1330, 1600, 1699, 2854 cm$^{-1}$.

(E)-2-[[4-(difluoromethoxy)-3,5-dimethoxyphenyl]-1-oxo-2-propenyl]amino]benzoic acid

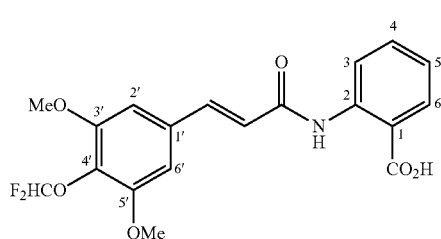

Piperidine (110 μL, 1.10 mmol) was added to a suspension of 4-(difluoromethoxy)-3,5-dimethoxybenzaldehyde (200 mg, 1.10 mmol) and 2-[(carboxyacetyl)amino]benzoic acid (233 mg, 1.05 mmol) in toluene (5.0 mL). The reaction flask was fitted with a Dean-Stark apparatus and heated to reflux for 30 min. The reaction was then cooled to rt and the resulting suspension was filtered and washed with toluene. The piperidinium salt was dissolved in MeOH (4 mL) and water (2 mL) and the solution was acidified with 20% aqueous AcOH. The crude product was collected by filtration and recrystallised from EtOH/water and filtered to afford (E)-2-[[4-(difluoromethoxy)-3,5-dimethoxyphenyl]-1-oxo-2-propenyl] amino]benzoic acid (210 mg, 51%) as a pale yellow crystalline solid; mp 211-215° C.; $\delta_H$ (400 MHz, DMSO-$d_6$) 3.87 (s, 6H, OCH$_3$), 6.87 (t, J=75 Hz, 1H, OCHF$_2$), 6.98 (d, J=15.6 Hz, 1H, CH=CHCO), 7.17 (s, 2H, H2', H6'), 7.18 (t, $J_{4,5}$=$J_{5,6}$=8.0 Hz, 1H, H5), 7.61 (d, J=15.6 Hz, 1H, CH=CHCO), 7.62 (t, $J_{3,4}$=$J_{4,5}$=8.0 Hz, 1H, H4), 8.00 (d, $J_{5,6}$=8.0 Hz, 1H, H6), 8.61 (d, $J_{3,4}$=8.0 Hz, 1H, H3), 11.33 (s, 1H, NH), 13.60 (s, 1H, CO$_2$H); $\delta_C$ (100 MHz, DMSO-$d_6$) 56.4, 105.5, 116.8 117.2 (t, J=259 Hz), 120.4, 122.9, 123.1, 129.6, 131.1, 132.9, 134.0, 140.8, 141.1, 152.6, 163.7, 169.4; $v_{max}$ 1153, 1113, 1224, 1506, 1593, 1694, 2602, 2946 cm$^{-1}$.

2-[(2-Carboxy-1-oxopropyl)amino]benzoic acid

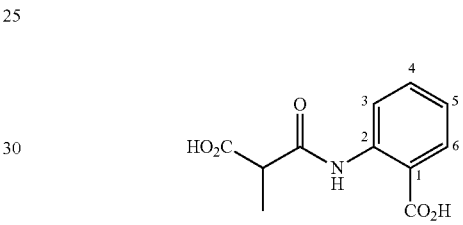

Anthranilic acid (1.00 g, 7.29 mmol) was added to a solution of 2,2,5-trimethyl-1,3-dioxane-4,6-dione (1.27 g, 8.02 mmol) in toluene (10 mL). The reaction flask was fitted with a Dean-Stark apparatus and the suspension was heated to reflux for 3 h. The suspension was cooled, filtered, washed with toluene and dried. 2-[(2-Carboxy-1-oxopropyl)amino] benzoic acid (1.46 g, 85%) was obtained as a colourless solid; $\delta_H$ (500 MHz, DMSO-$d_6$) 1.31 (d, J=7.2 Hz, 3H, CH$_3$), 3.52 (q, J=7.2 Hz, 1H, CH), 7.16 (t, $J_{3,4}$=$J_{4,5}$=8.0 Hz, 1H, H4), 7.59 (td, $J_{4,5}$=$J_{5,6}$=8.0, $J_{3,5}$=1.5 Hz, 1H, H5), 7.98 (dd, $J_{3,4}$=8.0, $J_{3,5}$=1.5 Hz, 1H, H3), 8.46 (d, $J_{5,6}$=8.0 Hz, 1H, H6), 11.36 (s, 1H, NH), 12.87 (br s, 1H, CO$_2$H), 13.52 (br s, 1H, CO$_2$H); $\delta_C$ (125 MHz, DMSO-$d_6$) 13.6, 48.4, 116.7, 120.0, 122.9, 131.1, 134.1, 140.5, 168.2, 169.4, 171.6. $v_{max}$ 1172, 1251, 1587, 1679, 2553, 2941, 2990, 3332 cm$^{-1}$.

(E)-2-[[3-(3,4-bis(difluoromethoxyl)phenyl-2-methyl-1-oxo-2-propenyl]amino]benzoic acid

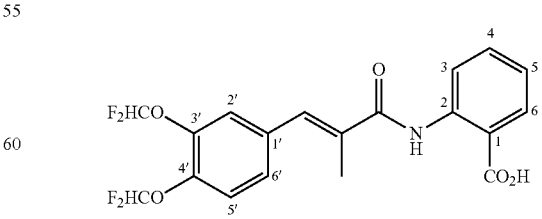

Piperidine (87 μL, 0.88 mmol) was added to a suspension of 3,4-bis(difluoromethoxy)benzaldehyde (210 mg, 0.88 mmol) and 2-[(2-carboxy-1-oxopropyl)amino]benzoic acid (199 mg, 0.84 mmol) in toluene (5.0 mL). The reaction flask was fitted with a Dean-Stark apparatus and heated to reflux for 30 min. The reaction was then cooled to rt and the resulting suspension was filtered and washed with toluene. The piperidinium salt was dissolved in MeOH (3 mL) and water (2 mL) and the solution was acidified with 20% aqueous AcOH. The crude product was collected by filtration and recrystallised from EtOH/water and filtered to afford (E)-2-[[3-(3,4-bis(difluoromethoxyl)phenyl-2-methyl-1-oxo-2-propenyl]amino]benzoic acid (130 mg, 37%) as a pale yellow crystalline solid; mp 151-153° C.; $\delta_H$ (500 MHz, DMSO-$d_6$) 3.87 (d, J=1.5 Hz, 3H, $CH_3$), 7.18 (t, $J_{4,5}=J_{5,6}=8.0$ Hz, 1H, H5), 7.25 (t, J=75 Hz, 1H, $OCHF_2$), 7.26 (t, J=75 Hz, 1H, $OCHF_2$), 7.41-7.48 (m, 3H, H2', H5', H6'), 7.63 (t, $J_{3,4}=J_{4,5}=8.0$ Hz, 1H, H4), 8.03 (d, $J_{5,6}=8.0$ Hz, 1H, H6), 8.66 (d, $J_{3,4}=8.0$ Hz, 1H, H3), 11.82 (s, 1H, NH), 13.72 (s, 1H, $CO_2H$); $\delta_C$ (125 MHz, DMSO-$d_6$) 13.9, 116.3 (t, J=259 Hz), 116.4 (t, J=259 Hz), 119.8, 120.8, 121.9, 122.8, 127.5, 131.2, 132.5, 133.7, 133.8, 134.2, 141.1, 141.3, 141.4, 166.5, 169.8; $\nu_{max}$ 1028, 1128, 1382, 1514, 1579, 1679, 3040 cm$^{-1}$.

6.94 (d, $J_{5',6'}=8.0$ Hz, 1H, H5'), 7.19 (dd, $J_{5',6'}=8.0$, $J_{2',6'}=2.0$ Hz, 1H, H6'), 7.35 (d, $J_{2',6'}=2.0$ Hz, 1H, H2'), (E)-N-(2-Aminophenyl)-[3-(3,4-bis(difluoromethoxyl)phenyl)]-2-propenamide

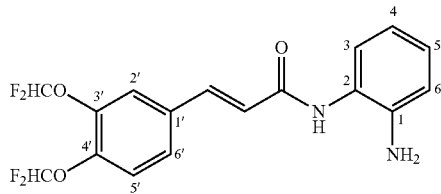

A suspension of (E)-3,4-bis(difluoromethoxy)phenyl-2-propenoic acid (0.16 g, 0.57 mmol) in $CH_2Cl_2$ (5 mL) was treated with oxalyl chloride (0.19 mL, 2.3 mmol) and catalytic DMF (1 drop). The solution was stirred at rt for 1 h and the solvent was removed under reduced pressure to give the acid chloride as a yellow solid. A solution of the acid chloride (0.57 mmol) in $CH_2Cl_2$ (10 mL) was added to a cooled solution of o-phenylenediamine (0.62 g, 0.63 mmol) in pyridine (5.0 mL) at 0° C. The suspension was stirred at 0° C. for 1 h, warmed to rt and stirred for 16 h and then acidified with 1 M HCl. The precipitate was collected by filtration providing (E)-2-[[3,4-bis(difluoromethoxy)phenyl)-1-oxo-2-propenyl]amino]-5-chloro-N-methylbenzamide (10 mg, 5%) as a brown crystalline solid; mp 140-142° C.; $\delta_H$ (500 MHz, DMSO-$d_6$) $\delta_H$ (500 MHz, DMSO-$d_6$) 5.03 (br s, 2H, $NH_2$), 6.56 (t, $J_{4,5}=J_{5,6}=8.0$ Hz, 1H, H4), 6.74 (d, $J_{5,6}=8.0$ Hz, 1H, H6), 6.89-6.92 (m, 3H, H5, CH=CHCO), 7.25 (t, J=74 Hz, 1H, $OCHF_2$), 7.26 (t, J=74 Hz, 1H, $OCHF_2$), 7.34 (d, $J_{5',6'}=8.0$ Hz, 1H, H5'), 7.40 (s, 1H, H2'), 7.52-7.59 (m, H3, H6', CH=CHCO), 9.41 (s, 1H, NH); $\delta_C$ (125 MHz, DMSO-$d_6$) 116.1, 116.3, 116.3 (t, J=259 Hz), 116.4 (t, J=259 Hz), 119.6, 121.1, 123.4, 123.7, 124.6, 125.8, 125.9, 133.3, 137.5, 141.4, 141.8, 142.4, 163.1; $\nu_{max}$ 755, 1036, 1261, 1502, 1615, 1656, 3221, 3371 cm$^{-1}$.

3,4-Bis(difluoromethoxy)acetophenone

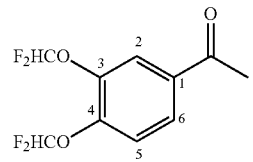

Methylmagnesium chloride (3 M in THF, 0.95 mL, 2.8 mmol) was added to a cooled solution of 3,4-bis(difluoromethoxy)benzaldehyde (0.45 g, 1.9 mmol) in anhydrous THF (30 mL) at 0° C. The solution was stirred at 0° C. for 1 h, warmed to rt and stirred for another 1 h. The solution was added to saturated aqueous $NH_4Cl$ and the aqueous phase was extracted with EtOAc. The combined organic fractions were washed with water, brine, dried and concentrated. The crude alcohol was dissolved in $CH_2Cl_2$ (25 mL) and 4 Å sieves (0.95 g) and PCC (0.61 g, 2.8 mmol) were added. The suspension was stirred at rt for 16 h and filtered through Celite. The crude product was purified by column chromatography, eluting with 10% EtOAc/petrol to give 3,4-bis(difluoromethoxy)acetophenone (0.41 g, 86%) as a colourless oil; $\delta_H$ (400 MHz, $CDCl_3$) 2.58 (s, 3H, $CH_3$), 6.58 (t, J=73 Hz, 1H, $OCHF_2$), 6.61 (t, J=73 Hz, 1H, $OCHF_2$), 7.32 (d, $J_{5,6}=8.0$ Hz, 1H, H5), 7.80-7.84 (m, 2H, H2, H6); $\delta_C$ (100 MHz, $CDCl_3$) 26.40, 115.3 (t, J=262 Hz), 115.5 (t, J=262 Hz), 121.1, 122.0, 126.9, 135.1, 141.9, 146.0 195.6; $\nu_{max}$ 1038, 1270, 1383, 1508, 1686, 2921, cm$^{-1}$.

(E)-Ethyl 3-(3,4-bis(difluoromethoxy)phenyl)-2-butenoate

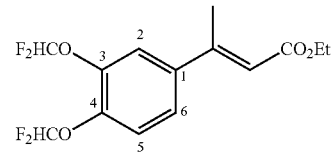 [SMILES: CCOC(=O)/C=C(\C)c1ccc(OC(F)F)c(OC(F)F)c1]

Triethyl phosphonoacetate (0.50 mL, 2.5 mmol) was added to a stirred suspension of 60% w/w NaH (0.10 g, 2.4 mmol) in anhydrous THF (5.0 mL). The suspension was stirred at rt for 30 min and a solution of 3,4-bis(difluoromethoxy)acetophenone (0.40 g, 1.5 mmol) in anhydrous THF (5.0 mL) was added to the reaction mixture. The solution was stirred at rt for 16 h and quenched with saturated aqueous $NH_4Cl$. The aqueous phase was extracted with EtOAc, washed with water, brine, dried and concentrated. The crude product was purified by column chromatography, eluting with 5% EtOAc/petrol to give (E)-ethyl 3-(3,4-bis(difluoromethoxy)phenyl)-2-butenoate (0.36 g, 70%) as a colourless oil; $\delta_H$ (400 MHz, $CDCl_3$) 1.31 (t, J=7.2 Hz, 3H, $CH_3$), 2.54 (s, 3H, $CH_3$), 4.21 (q, J=7.2 Hz, 2H, $CH_2$), 6.09 (m, 1H, C=CH), 6.54 (t, J=73 Hz, 2H, $OCHF_2$), 7.25 (d, $J_{5,6}=8.0$ Hz, 1H, H5), 7.32-7.35 (m, 2H, H2, H6); $\delta_C$ (100 MHz, $CDCl_3$) 14.3, 17.8, 60.1, 115.6 (t, J=262 Hz), 115.7 (t, J=262 Hz), 118.4, 120.7, 122.0, 124.6, 140.9, 142.0, 142.7, 152.7, 166.3; $\nu_{max}$ 1036, 1379, 1508, 1709, 2987 cm$^{-1}$.

(E)-3-(3,4-Bis(difluoromethoxy)phenyl)-2-butenoic acid

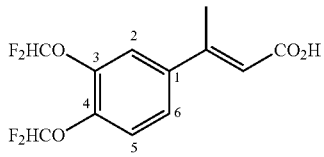

Aqueous 1.0 M NaOH (20 mL) was added to a solution of (E)-ethyl 3-(3,4-bis(difluoromethoxy)phenyl)-2-butenoate (0.36 g, 1.1 mmol) in EtOH (20 mL). The solution was stirred at rt for 16 h and then concentrated under reduced pressure to remove the EtOH. The aqueous phase was acidified with 1 M HCl and extracted with EtOAc, washed with water, brine, dried and concentrated. The crude product was recrystallised from EtOH/water to afford (E)-3-(3,4-dimethoxyphenyl)-2-butenoic acid (0.28 g, 85%) as a colourless crystalline solid; mp 73-74° C.; $\delta_H$ (500 MHz, CDCl$_3$) 2.60 (d, J=1.5 Hz, 3H, CH$_3$), 6.15 (q, J=1.5 Hz, 1H, C=CH), 6.55 (t, J=73 Hz, 2H, OCHF$_2$), 7.28 (d, J$_{5,6}$=8.0 Hz, 1H, H5), 7.36-7.38 (m, 2H, H2, H6); $\delta_C$ (125 MHz, CDCl$_3$) 18.2, 115.6 (t, J=262 Hz), 115.7 (t, J=262 Hz), 117.2, 120.9, 122.1, 124.7, 140.6, 142.1, 143.1, 155.7, 170.1; $\nu_{max}$ 1042, 1254, 1621, 1692, 2926 cm$^{-1}$.

(E)-2-[[3-(3,4-bis(difluoromethoxyl)phenyl)-1-oxo-2-butenyl]amino]benzoic acid

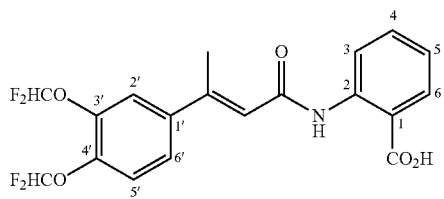

A suspension of (E)-3-(3,4-bis(difluoromethoxy)phenyl)-2-butenoic acid (0.12 g, 0.41 mmol) in CH$_2$Cl$_2$ (5 mL) was treated with oxalyl chloride (0.14 mL, 1.6 mmol) and catalytic DMF (1 drop). The solution was stirred at rt for 16 h and the solvent was removed under reduced pressure to give the acid chloride as a yellow solid. A solution of the acid chloride (0.41 mmol) in pyridine (2.0 mL) was added to a cooled solution of anthranilic acid (0.12 g, 0.63 mmol) in pyridine (1.0 mL) at 0° C. The suspension was stirred at 0° C. for 1 h, warmed to rt and stirred for 16 h and then acidified with 1 M HCl. The precipitate was collected by filtration and recrystallised from EtOH/water providing (E)-2-[[3-(3,4-bis(difluoromethoxyl)phenyl)-1-oxo-2-butenyl]amino]benzoic acid (35 mg, 21%) as a pale brown crystalline solid; mp 170-173° C.; $\delta_H$ (400 MHz, DMSO-d$_6$) 7.17 (t, J$_{3,4}$=J$_{4,5}$=8.0 Hz, 1H, H4), 7.25 (t, J=74 Hz, 1H, OCHF$_2$), 7.29 (t, J=74 Hz, 1H, OCHF$_2$), 7.39 (d, J$_{5',6'}$=8.0 Hz, 1H, H5'), 7.54 (d, J$_{5',6'}$=8.0, 1H, H6'), 7.56 (s, 1H, H2'), 7.60 (t, J$_{4,5}$=J$_{5,6}$=8.0 Hz, 1H, H5), 7.98 (d, J$_{3,4}$=8.0 Hz, 1H, H3), 8.50 (d, J$_{5,6}$=8.0 Hz, 1H, H6), 11.19 (s, 1H, NH); $\delta_C$ (100 MHz, DMSO-d$_6$) 17.0, 116.4 (t, J=258 Hz), 116.6 (t, J=258 Hz), 117.2, 119.0, 120.4, 120.8, 121.7, 122.9, 124.4, 131.1, 133.9, 139.9, 140.6, 141.6, 142.1, 149.1, 164.3, 169.3; $\nu_{max}$ 768, 1058, 1116, 1379, 1508, 1585, 1683, 3175 cm$^{-1}$.

The details of specific embodiments described in this invention are not to be construed as limitations. Various equivalents and modifications may be made without departing from the essence and scope of this invention, and it is understood that such equivalent embodiments are part of this invention.

The invention claimed is:
1. A compound of Formula (I)

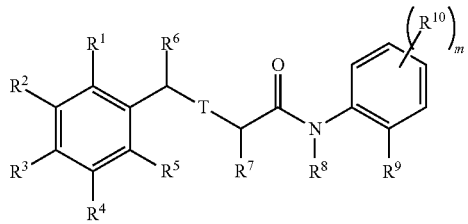

Formula (I)

or a pharmaceutically acceptable salt or prodrug thereof, wherein:
T is a single bond, a double bond or a triple bond;
R$^1$, R$^4$, and R$^5$ are each independently selected from the group consisting of: H, halogen, OH, NO$_2$, CN, NH$_2$, optionally substituted C$_1$-C$_{12}$ alkyl, optionally substituted C$_2$-C$_{12}$ alkenyl, optionally substituted C$_2$-C$_{12}$ alkynyl, optionally substituted C$_1$-C$_{10}$ heteroalkyl, optionally substituted C$_3$-C$_{12}$ cycloalkyl, optionally substituted C$_3$-C$_{12}$ cycloalkenyl, optionally substituted C$_2$-C$_{12}$ heterocycloalkyl, optionally substituted C$_2$-C$_{12}$ heterocycloalkenyl, optionally substituted C$_6$-C$_{18}$ aryl, optionally substituted C$_1$-C$_{18}$ heteroaryl, optionally substituted C$_1$-C$_{12}$ alkyloxy, optionally substituted C$_2$-C$_{12}$ alkenyloxy, optionally substituted C$_2$-C$_{12}$ alkynyloxy, optionally substituted C$_1$-C$_{10}$ heteroalkyloxy, optionally substituted C$_3$-C$_{12}$ cycloalkyloxy, optionally substituted C$_3$-C$_{12}$ cycloalkenyloxy, optionally substituted C$_1$-C$_{12}$ heterocycloalkyloxy, optionally substituted C$_1$-C$_{12}$ heterocycloalkenyloxy, optionally substituted C$_6$-C$_{18}$ aryloxy, optionally substituted C$_1$-C$_{18}$ heteroaryloxy, optionally substituted C$_1$-C$_{12}$ alkylamino, SR$^{11}$, SO$_3$H, SO$_2$NR$^{11}$R$^{12}$, SO$_2$R$^{11}$, SONR$^{11}$R$^{12}$, SOR$^{11}$, COR$^{11}$, COOH, COOR$^{11}$, CONR$^{11}$R$^{12}$, NR$^{11}$COR$^{12}$, NR$^{11}$COOR$^{12}$, NR$^{11}$SO$_2$R$^{12}$, NR$^{11}$CONR$^{12}$R$^{13}$, NR$^{11}$R$^{12}$, and acyl;
at least one of R$^2$ and R$^3$ is selected from the group consisting of C$_1$-C$_{12}$ alkyloxy containing at least one halogen atom, C$_2$-C$_{12}$ alkenyloxy containing at least one halogen atom, C$_2$-C$_{12}$ alkynyloxy containing at least one halogen atom, and C$_3$-C$_{12}$ cycloalkyloxy containing at least one halogen atom and the other R$^2$ or R$^3$ is selected from the group consisting of optionally substituted C$_1$-C$_{12}$ alkyloxy, optionally substituted C$_2$-C$_{12}$ alkenyloxy, optionally substituted C$_2$-C$_{12}$ alkynyloxy and optionally substituted C$_3$-C$_{12}$ cycloalkyloxy; or R$^2$ and R$^3$ are combined to form —O—X—O— where X is optionally substituted C$_{1-12}$ alkyl containing at least one halogen atom;
wherein at least one of R$^1$, R$^2$, R$^3$, R$^4$, and R$^5$ is the group —O—CHF$_2$;
R$^6$ and R$^7$ are present when T is a single bond or a double bond but not when T is a triple bond, each R$^6$ and R$^7$ being independently selected from the group consisting of: H, NO$_2$, CN, optionally substituted C$_1$-C$_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$ $NR^{11}SO_2R^{12}$, $NR^{11}CONR^{12}R^{13}$, $NR^{11}R^{12}$, and acyl;

$R^8$ is selected from the group consisting of: H, a N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^9$ is COOH;

$R^{10}$ is selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl;

each $R^{11}$, $R^{12}$ and $R^{13}$ is independently selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl; and m is an integer selected from the group consisting of 0, 1, 2, 3, and 4.

2. A compound as claimed in claim 1, wherein at least one of $R^1$, $R^2$, and $R^5$ is selected from the group consisting of $C_1$-$C_{12}$ alkyloxy containing at least one halogen atom, $C_2$-$C_{12}$ alkenyloxy containing at least one halogen atom, and $C_2$-$C_{12}$ alkynyloxy containing at least one halogen atom.

3. A compound as claimed in claim 2, wherein at least one of $R^1$, $R^2$, $R^3$, $R^4$ and $R^5$ has the Formula (II);

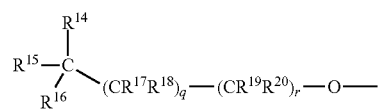

Formula (II)

wherein:
$R^{14}$, $R^{15}$, and $R^{16}$ are each independently selected from the group consisting of: H, halogen, OH, $NO_2$, CN, $NH_2$, optionally substituted $C_1$-$C_{12}$ alkyl, and optionally substituted $C_2$-$C_{12}$ alkenyl;
$R^{17}$, $R^{18}$, $R^{19}$, and $R^{20}$ are each independently selected from the group consisting of: H, halogen, OH, $NO_2$, CN, and $NH_2$;
at least one of $R^{14}$, $R^{15}$, $R^{16}$, $R^{17}$, $R^{18}$, $R^{19}$, and $R^{20}$ is or contains a halogen atom;
q is an integer selected from the group consisting of 0, 1, 2, 3, 4, 5, 6, 7, 8, 9, and 10; and
r is an integer selected from the group consisting of 0, 1, 2, 3, 4, 5, 6, 7, 8, 9, and 10.

4. A compound as claimed in claim 3, wherein q and r are 0, and at least two of $R^{14}$, $R^{15}$, and $R^{16}$ are a halogen.

5. A compound as claimed in claim 1, wherein the halogen is fluorine.

6. A compound as claimed in claim 1, wherein at least $R^2$ and $R^3$ are the group —O—$CHF_2$.

7. A compound as claimed in claim 1, wherein T is a double bond or a triple bond.

8. A compound as claimed in claim 1, wherein $R^{10}$ is halogen.

9. A compound as claimed in claim 1, wherein m is 1.

10. A compound of Formula (III)

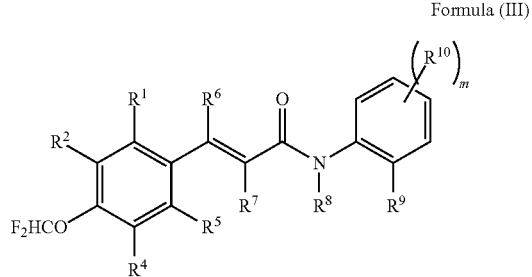

Formula (III)

or a pharmaceutically acceptable salt or prodrug thereof, wherein:
$R^1$, $R^4$, and $R^5$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl; provided that at least one of $R^1$, $R^2$, $R^4$, and $R^5$ contains a halogen atom;

$R^2$ is selected from the group consisting of optionally substituted $C_1$-$C_{12}$ alkyloxy containing at least one halogen atom, optionally substituted $C_2$-$C_{12}$ alkenyloxy, optionally substituted $C_2$-$C_{12}$ alkynyloxy and optionally substituted $C_3$-$C_{12}$ cycloalkyloxy;

$R^6$ and $R^7$ are each independently selected from the group consisting of: H, $NO_2$, CN, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^1SO_2R^{12}$, $NR^{11}CONR^{12}R^{13}$, $NR^{11}R^{12}$, and acyl $R^8$ is selected from the group consisting of: H, a N-protecting group, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{10}$heteroalkyl, optionally substituted $C_3$-$C_{12}$cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$aryl, and optionally substituted $C_1$-$C_{18}$heteroaryl;

$R^9$ is COOH, $R^{10}$ is selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl;

each $R^{11}$, $R^{12}$ and $R^{13}$ is independently selected from the group consisting of H, optionally substituted $C_1$-$C_{12}$alkyl, optionally substituted $C_2$-$C_{12}$alkenyl, optionally substituted $C_2$-$C_{12}$alkynyl, optionally substituted $C_1$-$C_{10}$heteroalkyl, optionally substituted $C_3$-$C_{12}$cycloalkyl, optionally substituted $C_3$-$C_{12}$cycloalkenyl, optionally substituted $C_1$-$C_{12}$ heterocycloalkyl, optionally substituted $C_1$-$C_{12}$ heterocycloalkenyl, optionally substituted $C_6$-$C_{18}$aryl, and optionally substituted $C_{1-18}$heteroaryl; and m is an integer selected from the group consisting of 0, 1, 2, 3, and 4.

11. A compound as claimed in claim 10, wherein $R^2$ is the group —O—$CHF_2$.

12. A compound as claimed in claim 10, wherein $R^2$ is selected from the group consisting of: optionally substituted $C_1$-$C_{12}$ alkyloxy containing at least one halogen atom and optionally substituted $C_2$-$C_{12}$ alkynyloxy.

13. A compound as claimed in claim 10, wherein $R^1$ is the group —O—$CHF_2$.

14. A compound as claimed in claim 10, wherein $R^4$ is the group —O—$CHF_2$.

15. A compound as claimed in claim 10, wherein $R^5$ is the group —O—$CHF_2$.

16. A compound as claimed in claim 10, wherein $R^4$ is selected from the group consisting of: optionally substituted $C_1$-$C_{12}$ alkyloxy and optionally substituted $C_2$-$C_{12}$ alkynyloxy.

17. A compound as claimed in claim 10, wherein $R^6$ and $R^7$ are each independently selected from the group consisting of: H, and optionally substituted $C_1$-$C_{12}$ alkyl.

18. A compound of Formula (V)

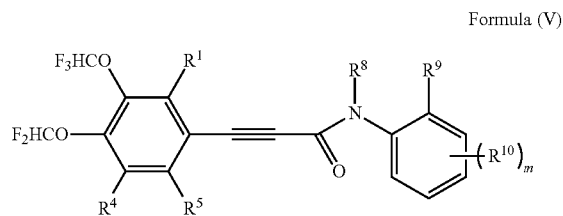

Formula (V)

or a pharmaceutically acceptable salt or prodrug thereof, wherein:

$R^1$, $R^4$, and $R^5$ are each independently selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl; provided that at least one of $R^1$, $R^2$, $R^3$, $R^4$, and $R^5$ contains a halogen atom;

$R^8$ is selected from the group consisting of: H, an N-protecting group, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl;

$R^9$ is selected from the group consisting of: $COOR^{11}$, $CONR^{11}R^{12}$, and $NR^{11}R^{12}$;

$R^{10}$ is selected from the group consisting of: H, halogen, OH, $NO_2$, CN, $NH_2$, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_2$-$C_{12}$ heterocycloalkyl, optionally substituted $C_2$-$C_{12}$ heterocycloalkenyl, optionally substituted $C_6$-$C_{18}$ aryl, optionally substituted $C_1$-$C_{18}$ heteroaryl, optionally substituted $C_1$-$C_{12}$ alkyloxy, optionally substituted $C_2$-$C_{12}$ alkenyloxy, optionally substituted $C_2$-$C_{12}$ alkynyloxy, optionally substituted $C_1$-$C_{10}$ heteroalkyloxy, optionally substituted $C_3$-$C_{12}$ cycloalkyloxy, optionally substituted $C_3$-$C_{12}$ cycloalkenyloxy, optionally substituted $C_1$-$C_{12}$ heterocycloalkyloxy, optionally substituted $C_1$-$C_{12}$ heterocycloalkenyloxy, optionally substituted $C_6$-$C_{18}$ aryloxy, optionally substituted $C_1$-$C_{18}$ heteroaryloxy, optionally substituted $C_1$-$C_{12}$ alkylamino, $SR^{11}$, $SO_3H$, $SO_2NR^{11}R^{12}$, $SO_2R^{11}$, $SONR^{11}R^{12}$, $SOR^{11}$, $COR^{11}$, $COOH$, $COOR^{11}$, $CONR^{11}R^{12}$, $NR^{11}COR^{12}$, $NR^{11}COOR^{12}$, $NR^{11}SO_2R^{12}$, $NR^{11}CONR^{12}R^{13}$, $NR^{11}R^{12}$, and acyl;

each $R^{11}$, $R^{12}$ and $R^{13}$ is independently selected from the group consisting of H, optionally substituted $C_1$-$C_{12}$ alkyl, optionally substituted $C_2$-$C_{12}$ alkenyl, optionally substituted $C_2$-$C_{12}$ alkynyl, optionally substituted $C_1$-$C_{10}$ heteroalkyl, optionally substituted $C_3$-$C_{12}$ cycloalkyl, optionally substituted $C_3$-$C_{12}$ cycloalkenyl, optionally substituted $C_1$-$C_{12}$ heterocycloalkyl, optionally substituted $C_1$-$C_{12}$ heterocycloalkenyl, optionally substituted $C_6$-$C_{18}$ aryl, and optionally substituted $C_1$-$C_{18}$ heteroaryl; and m is an integer selected from the group consisting of 0, 1, 2, 3, and 4.

19. A compound as claimed in claim 1 selected from the group consisting of:

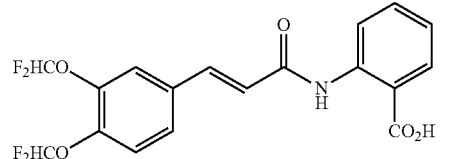

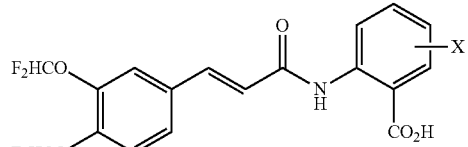

X = Cl, Br

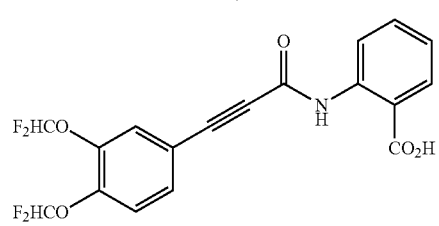

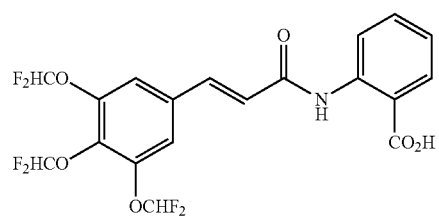

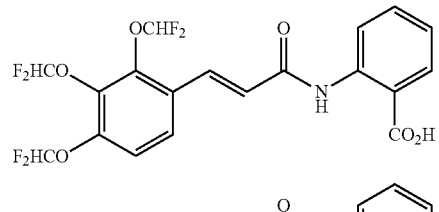

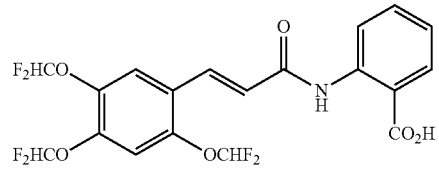

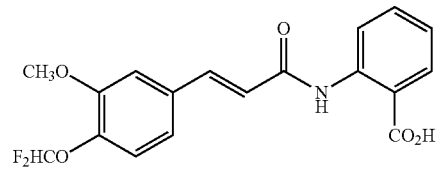

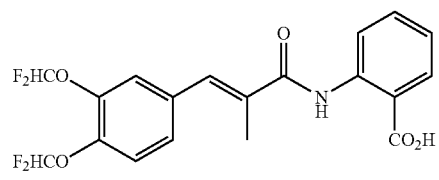

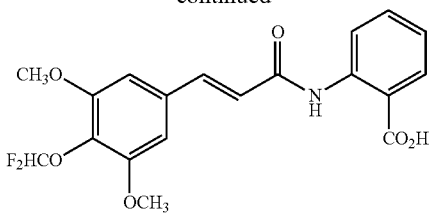
or a pharmaceutically acceptable salt or prodrug thereof.
* * * * *

UNITED STATES PATENT AND TRADEMARK OFFICE
CERTIFICATE OF CORRECTION

| | | |
|---|---|---|
| PATENT NO. | : 8,624,056 B2 | Page 1 of 1 |
| APPLICATION NO. | : 12/809751 | |
| DATED | : January 7, 2014 | |
| INVENTOR(S) | : Darren James Kelly et al. | |

It is certified that error appears in the above-identified patent and that said Letters Patent is hereby corrected as shown below:

In the Claims

At column 40, claim 18, lines 46-52, please correct the chemical formula to display an "$F_2HCO$" instead of "$F_3HCO$" so the chemical formula is displayed as follows:

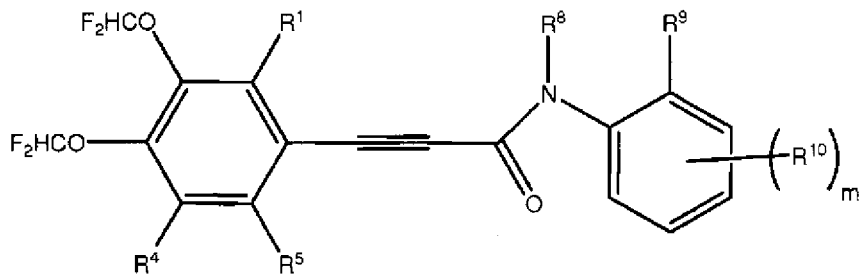

Signed and Sealed this
First Day of April, 2014

Michelle K. Lee
*Deputy Director of the United States Patent and Trademark Office*